(12) United States Patent
Padula et al.

(10) Patent No.: US 11,253,149 B2
(45) Date of Patent: Feb. 22, 2022

(54) HOLOGRAPHIC REAL SPACE REFRACTIVE SEQUENCE

(71) Applicant: Veyezer LLC, Killingworth, CT (US)

(72) Inventors: William V. Padula, Killingworth, CT (US); Teddi R. Dinsmore, Killingworth, CT (US)

(73) Assignee: Veyezer, LLC, Guilford, CT (US)

( * ) Notice: Subject to any disclaimer, the term of this patent is extended or adjusted under 35 U.S.C. 154(b) by 275 days.

(21) Appl. No.: 16/593,619

(22) Filed: Oct. 4, 2019

(65) Prior Publication Data

US 2020/0113434 A1  Apr. 16, 2020

Related U.S. Application Data

(63) Continuation-in-part of application No. 15/904,995, filed on Feb. 26, 2018, now Pat. No. 10,441,161.

(51) Int. Cl.
*A61B 3/103* (2006.01)
*G02B 27/01* (2006.01)
(Continued)

(52) U.S. Cl.
CPC .............. *A61B 3/103* (2013.01); *A61B 3/005* (2013.01); *A61B 3/0033* (2013.01); *A61B 3/08* (2013.01);
(Continued)

(58) Field of Classification Search
CPC ........... A61B 3/103; A61B 3/005; A61B 3/08; A61B 3/0033; A61B 3/028;
(Continued)

(56) References Cited

U.S. PATENT DOCUMENTS

| 5,002,364 A | 3/1991 | Steenblik |
| 5,299,454 A | 4/1994 | Fuglewicz et al. |

(Continued)

FOREIGN PATENT DOCUMENTS

| CN | 105662334 A | 6/2016 |
| CN | 107592798 A | 1/2018 |
| DE | 3405778 A1 | 8/1985 |

OTHER PUBLICATIONS

Barnett et al., Vision concerns after mild traumatic brain injury. Curr Treat Options Neurol. Feb. 2015;17(2):329, 14 pages.
(Continued)

*Primary Examiner* — Tuyen Tra
(74) *Attorney, Agent, or Firm* — McCarter & English, LLP

(57) ABSTRACT

A system and a method for holographic eye testing device are disclosed. The system renders one or more three dimensional objects within the holographic display device. The system updates the rendering of the one or more three dimensional objects within the holographic display device, by virtual movement of the one or more three dimensional objects within the level of depth. The system receives input from a user indicating alignment of the one or more three dimensional objects after the virtual movement. The system determines a delta between a relative virtual position of the one or more three dimensional objects at the moment of receiving input and an optimal virtual position and generates prescriptive remedy based on the delta.

20 Claims, 17 Drawing Sheets

(51) Int. Cl.
*A61B 3/00* (2006.01)
*A61B 3/08* (2006.01)

(52) U.S. Cl.
CPC ..... *G02B 27/0103* (2013.01); *G02B 27/0172* (2013.01); *G02B 2027/0174* (2013.01)

(58) Field of Classification Search
CPC .... G02B 2027/0174; G02B 2027/0198; G02B 2027/0187; G02B 2027/014; G02B 27/017; G02B 27/0103; G02B 27/0172
See application file for complete search history.

(56) References Cited

U.S. PATENT DOCUMENTS

| | | | |
|---|---|---|---|
| 5,452,030 | A | 9/1995 | Feinbloom |
| 5,491,492 | A | 2/1996 | Knapp et al. |
| 5,579,158 | A | 11/1996 | Padula |
| 6,007,569 | A | 12/1999 | Frenkel et al. |
| 6,099,124 | A | 8/2000 | Hidaji |
| 6,231,527 | B1 | 5/2001 | Sol |
| 6,357,889 | B1 | 3/2002 | Duggal et al. |
| 6,676,284 | B1 | 1/2004 | Wynne Willson |
| 7,014,336 | B1 | 3/2006 | Ducharme et al. |
| 7,253,824 | B2 | 8/2007 | Medes et al. |
| 7,374,284 | B2 | 5/2008 | Peli |
| 7,549,743 | B2 | 6/2009 | Huxlin et al. |
| 7,789,508 | B2 | 9/2010 | Padula, I et al. |
| 8,262,590 | B2 | 9/2012 | Padula |
| 8,472,120 | B2 * | 6/2013 | Border ............... G02B 27/0093 359/630 |
| 8,477,425 | B2 * | 7/2013 | Border .................... G06F 1/163 359/630 |
| 8,488,246 | B2 * | 7/2013 | Border .................... G06F 3/013 359/630 |
| 8,567,950 | B2 | 10/2013 | Padula |
| 9,101,312 | B2 | 8/2015 | Waldorf et al. |
| 10,441,161 | B2 | 10/2019 | Padula et al. |
| 10,593,092 | B2 * | 3/2020 | Solomon ................. G06F 3/013 |
| 2005/0195598 | A1 | 9/2005 | Dancs et al. |
| 2005/0248723 | A1 | 11/2005 | Mohan |
| 2006/0264786 | A1 | 11/2006 | Nashner |
| 2009/0137933 | A1 | 5/2009 | Lieberman et al. |
| 2009/0240170 | A1 | 9/2009 | Rowley et al. |
| 2010/0035727 | A1 | 2/2010 | Brunner |
| 2013/0194389 | A1 | 8/2013 | Vaught et al. |
| 2013/0201446 | A1 | 8/2013 | Hall et al. |
| 2016/0216515 | A1 | 7/2016 | Bouchier et al. |
| 2016/0270656 | A1 | 9/2016 | Samec |
| 2017/0000326 | A1 | 1/2017 | Samec et al. |

OTHER PUBLICATIONS

Cooper et al., Reduction of asthenopia after accommodative facility training. Am J Optom Physiol Opt. Jun. 1987;64(6):430-6.
Cooper et al., Reduction of asthenopia in patients with convergence insufficiency after fusional vergence training. Am J Optom Physiol Opt. Dec. 1983;60(12):982-9.
Daum, Predicting results in the orthoptic treatment of accommodative dysfunction. Am J Optom Physiol Opt. Mar. 1984;61(3):184-9.
Kafaligonul et al., Feedforward and feedback processes in vision. Front Psychol. Mar. 12, 2015;6:279, 3 pages.
Lamme et al., Feedforward, horizontal, and feedback processing in the visual cortex. Curr Opin Neurobiol. Aug. 1998;8(4):529-35.
Lamme et al., The distinct modes of vision offered by feedforward and recurrent processing. Trends Neurosci. Nov. 2000;23(11):571-9.
Liebowitz, The two modes of processing concept and some implications. Organization and Representation in Perception. Jacob Beck (Ed.), Lawrence Erlbaum Associates, Hillsdale, New Jersey. Chapter 17, pp. 343-363. (1982).
Neurolens, Headaches, Neck Pain, Eye Strain, It may be a misalignment in your vision. Retrieved online at: https://www.neurolenses.com/about-US/ eyeBrain Medical, Inc. 6 pages. Feb. 2009.
Padula et al., Evaluating and Treating Visual Dysfunction. Brain Injury Medicine, Principles and Practice, Second Edition. Demos Medical Publishing LLC, New York. Nathan D. Zasler (Ed.). pp. 750-768, (2013).
Padula et al., Evaluating and treating visual dysfunction. Brain Injury Medicine. Zasler (Ed.), Demos Medical Publishing. pp. 511-528, (2007).
Padula et al., Post trauma vision syndrome and visual midline shift syndrome. NeuroRehabilitation. 1996;6(3):165-71.
Padula et al., Risk of fall (RoF) intervention by affecting visual egocenter through gait analysis and yoked prisms. NeuroRehabilitation. 2015;37(2):305-14.
Silver, Textbook of Traumatic Brain Injury, 2nd Edition. American Psychiatric Publishing, Inc., (2005).
Trevarthen et al., Perceptual unity of the ambient visual field in human commissurotomy patients. Brain. Sep. 1973;96(3):547-70.
U.S. Appl. No. 15/904,995, filed Feb. 26, 2018, U.S. Pat. No. 10,441,161, Issued.
U.S. Appl. No. 10/713,912, filed May 2, 2003, U.S. Pat. No. 7,253,824, Issued.
U.S. Appl. No. 11/818,957, filed Nov. 18, 2005, U.S. Pat. No. 7,789,508, Issued.
U.S. Appl. No. 12/798,264, filed Apr. 1, 2010, U.S. Pat. No. 8,262,590, Issued.
U.S. Appl. No. 12/653,139, filed Dec. 9, 2009, U.S. Pat. No. 8,567,950, Issued.
Avudainayagam et al., A Test for Progressive Myopia and the Role of Latent Accommodation in its Development. Int J Ophthalmol Clin Res. Apr. 10, 2015;2(2):1-7.
Basford et al., An assessment of gait and balance deficits after traumatic brain injury. Arch Phys Med Rehabil. Mar. 2003;84(3):343-9.
Benabib et al., Efficiency in visual skills and postural control: A dynamic interaction. Occup Ther Pract. 1993;3:57-60.
Dickstein et al., Light touch and center of mass stability during treadmill locomotion. Gait Posture. Aug. 2004;20(1):41-7.
Eye Focus, Vision Testing with a Hologram, Holographic Technology. Retrieved online at: http://www.eyefocus.com.au/common/node/10. 7 pages Jan. 2011.
Hubel et al., Receptive fields of single neurones in the cat's striate cortex. J Physiol. Oct. 1959;148(3):574-91.
Liebowiiz, The two modes of processing concept and some implications. Organization and Representation in Perception. Jacob Beck (Ed.), Lawrence Erlbaum Associates, Hillsdale, New Jersey. Chapter 17, pp. 343-363. (1982).
Padula et al., Post-Trauma Vision Syndrome: Part II. Visual Midline Shift Syndrome, (1996).
Padula et al., Visual evoked potentials (VEP) evaluating treatment for post-trauma vision syndrome (PTVS) in patients with traumatic brain injuries (TBI). Brain Inj. Feb.-Mar. 1994;8(2):125-33.
Padula, Neuro-visual processing rehabilitation: An intergrated model of service. Santa Ana, CA: Optometric Extension Program Foundation Press. (2012).
Peli, Field expansion for homonymous hemianopia by optically induced peripheral exotropia. Optom Vis Sci. Sep. 2000;77(9):453-64.
The N.I.R.E., Vision Aids for People Having Homonymous Hemianopsia. The National Institute for Rehabilitation Engineering (NIRE). 7 pages, 2001.
Trevarthen, Two mechanisms of vision in primates. Psychol Forsch. 1968;31(4):299-348.
Extended European Search Report dated Oct. 19, 2021 for Application No. 19757833.9.

* cited by examiner

HOLOGRAPHIC REAL SPACE REFRACTIVE SEQUENCE

CROSS-REFERENCE TO RELATED APPLICATION

This application is a continuation-in-part of U.S. patent application Ser. No. 15/904,995, filed on Feb. 26, 2018. The prior application is incorporated herein by reference in its entirety.

BACKGROUND

1. Technical Field

Systems and methods for providing a visual examination using holographic projection in real space and time are provided.

2. Background Art

For over one hundred years, doctors have provided eye examinations including refraction by using lenses and prisms to determine the refractive state and binocularity of the patient. Refraction means to bend light. Persons with myopia (nearsightedness), hyperopia (farsightedness) and astigmatism (two different power curves) performed a refraction to correct the refractive state and blurred vision of the patient by using physical lenses and prisms. While in the 19th century the refraction was mostly conducted with a trial frame by holding up individual lenses before each eye to make the image more clear, in the 20th century the phoropter (meaning "many lenses") was developed. This instrument was extended on the arm of a physical stand and the instrument was positioned before the patient's face. The clinician would then turn the dial to move different lenses in front of the person's eyes to find the best subjective refraction to improve distance vision. The instrument was then advanced to include prisms that could be used to disassociate images or change the position of the image enabling the clinician the ability to evaluate muscle ranges and the ability to maintain eye alignment and binocularity. It also permitted assessment of the person's ability to accommodate or focus at a near range. This was all for the purpose of designing glasses to improve eyesight and visual acuity for both distance and near ranges as well as to prescribe prisms to correct for imbalance in eye alignment affecting binocularity.

While the phoropter is an effective instrument and still used today, it limits the peripheral field and cannot assess binocularity in any other meridian other than primary gaze or looking straight ahead. Binocular imbalances can sometimes only be represented with gaze outside of the primary gaze position. Therefore, the instrument has limited value for these purposes and/or lead the clinician to only be able to prescribe lenses and prisms for one position of the eyes. In addition, the large phoropter blocks the peripheral vision producing an abnormal environment and restriction of side vision, which frequently affects the intensity of the attentional visual process and cause the refractive correction to be too strong or imbalanced.

These and other issues and limitations of existing instruments and technologies are addressed and overcome by the systems and methods of the present disclosure.

SUMMARY OF THE INVENTION

Described herein is a system to evaluate the refractive state of the eye and visual process as well as binocularity in the nine cardinal positions of gaze while in real space by using holographic projection for each eye. The refractive state assessment has been designed to enable the eye of the patient to focus on virtual objects in the manner that the refractive imbalance will focus to maintain clear vision. For example, a object is presented with three dimensions. The myopic eye will focus on the near side of the object and see it with clarity. The dimensions and position of the object is then moved to refocus the far or distance side of the object and calibration is determined as to the power of the eye and the power of the lens required to re-focus the eye to best visual acuity at infinity. The same would occur for the hyperopic eye, only the far portion of the three-dimensional object will be in initial focus.

The patient uses hand movements and/or voice command to communicate the subjective measurement of the dioptric power to correct the vision to best visual acuity and, advantageously, these objectives are accomplished through manipulation of the object in real space. More particularly, in an exemplary embodiment of the present disclosure, an eye with astigmatism would be presented a three dimensional object where perpendicular lines would enable the patient to observe that one of the lines is clear and the other blurred. The object will be rotated to determine the axis of the astigmatism and then the opposite or blurred side of the object would be shifted in space virtually to bring it into focus. This sequence of operation will provide the amount of astigmatism measured in this eye and therefore the predicted amount of cylindrical correction needed to bring clarity. If the patient has both myopia or hyperopia and astigmatism, the object would be simultaneously be manipulated to determine myopia or hyperopia while also evaluation the dioptric power of the astigmatism.

Additional features, functions and benefits of the disclosed systems and methods will be apparent from the detailed description which follows, particularly when read in conjunction with the accompanying figures.

BRIEF DESCRIPTION OF DRAWINGS

Illustrative embodiments are shown by way of example in the accompanying drawings and should not be considered as a limitation of the present disclosure.

DETAILED DESCRIPTION

Apparatus, methods, and non-transitory computer readable medium are described for a holographic eye testing device. Example embodiments provide a device for utilizing holographic virtual projection to perform eye testing, diagnosis, and prescriptive remedy.

In some embodiments, the disclosed holographic eye testing device renders on a head mounted device, one or more three dimensional objects within the holographic display device, wherein the rendering corresponds to a virtual level of depth viewable by a user. The holographic display device updates the rendering of the one or more three dimensional objects, wherein the updates include a virtual movement of the one or more three dimensional objects within the virtual level of depth. The holographic display device receives input from a user, wherein the input includes an indication of alignment of the one or more three dimensional objects based on the virtual movement. The indication of alignment includes a relative position between the one or more three dimensional objects. The holographic display device determines a delta between the relative virtual position between the one or more three dimensional objects and an optimal virtual position. The holographic display device generates prescriptive remedy based on the delta.

Figure 1:
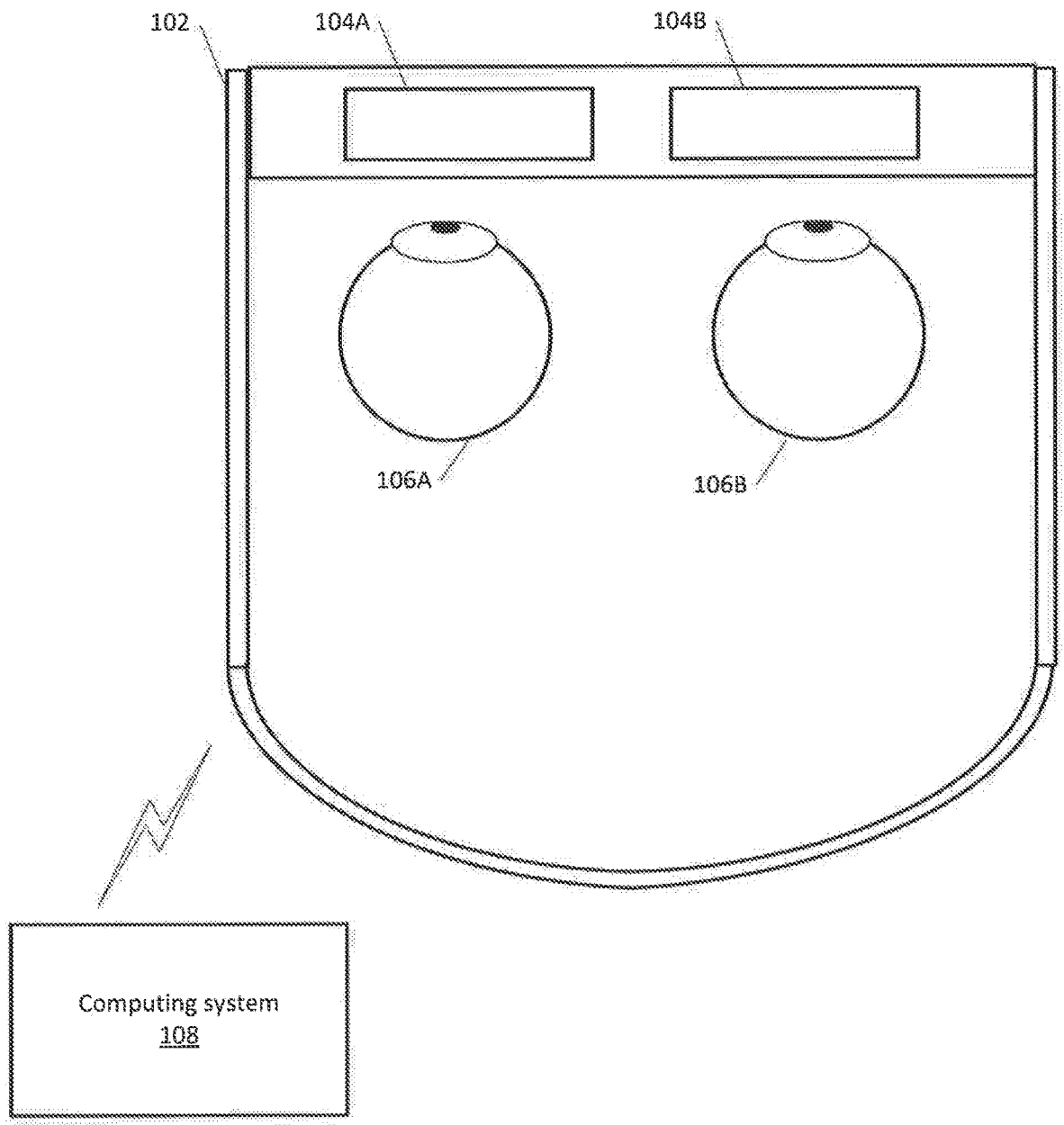
FIG. 1 is a block diagram illustrating a system for the holographic eye testing device according to an exemplary embodiment.

FIG. 1 is a block diagram illustrating a system 100 for the holographic eye testing device according to an exemplary embodiment. In one embodiment, the holographic eye testing device can include a head mounted display (HMD) 102. The HMD 102 can include a pair of combiner lenses 104A, 104B for rendering three dimensional (3D) images within a user's field of view (FOV). The combiner lenses 104A, 104B can be calibrated to the interpupillary distance from the user's eyes 106A, 106B. A computing system 108 can be connected to the combiner lenses 104A, 104B. The holographic eye testing device can be repositioned in any of the nine primary gaze positions as needed. These tests are built to run on technical platforms that can project 3D holographic images within a field of view provided by a wired or wireless headset. The HMD 102 can be connected to an adjustable, cushioned inner headband, which can tilt the combiner lenses 104A, 104B up and down, as well as forward and backward. To wear the unit, the user fits the HMD 102 on their head, using an adjustment wheel at the back of the headband to secure it around the crown, supporting and distributing the weight of the unit equally for comfort, before tilting the visor and combiner lenses 104A, 104B towards the front of the eyes.

The computing system 108 can be inclusive to the HMD 102, where the holographic eye testing device is a self contained apparatus. The computing system 108 in the self contained apparatus can include additional power circuitry to provide electrical current to the parts of the computing system 108. Alternatively, the computing system 108 can be external to the HMD 102 and communicatively coupled either through wired or wireless communication channels to the HMD 102. Wired communication channels can include digital video transmission formats including High Definition Multimedia Interface (HDMI), DisplayPort™ (DisplayPort is a trademark of VESA of San Jose Calif., U.S.A.), or any other transmission format capable of propagating a video signal from the computing system 108 to the combiner lenses 104A, 104B. Additionally, the HMD 102 can include speakers or headphones for the presentation of instructional audio to the user during the holographic eye tests. In a wireless communication embodiment, the HMD 102 can include a wireless adapter capable of low latency high bandwidth applications, including but not limited to IEEE 802.11ad. The wireless adapter can interface with the computing system 108 for the transmission of low latency video to be displayed upon the combiner lenses 104, 104B.

Additionally the computing system 108 can include software for the manipulation and rendering of 3D objects within a virtual space. The software can include both platform software to support any fundamental functionality of the HMD 102, such as motion tracking, input functionality, and eye tracking. Platform software can be implemented in a virtual reality (VR) framework, augmented reality (AR) framework, or mixed reality (MR) framework. Platform software to support the fundamental functionality can include but are not limited to SteamVR® (SteamVR is a registered trademark of the Valve Corporation, Seattle Wash., U.S.A) software development kit (SDK), Oculus® VR SDK (Oculus is a registered trademark of Oculus VR LLC, Irvine Calif., U.S.A.), OSVR (Open source VR) (OSVR is a registered trademark of Razer Asia Pacific Pte. Ltd. Singapore) SDK, and Microsoft Windows Mixed Reality Computing Platform. Application software executing on the computing system 108 with the underlying platform software can be a customized rendering engine, or an off-the-shelf 3D rendering framework, such as Unity® Software (Unity Software is a registered trademark of Unity Technologies of San Francisco Calif., U.S.A). The rendering framework can provide the basic building blocks of the virtualized environment for the holographic refractive eye test, including 3D objects and manipulation techniques to change the appearance of the 3D objects. The rendering framework can provide application programming interfaces (APIs) for the instantiation of 3D objects and well-defined interfaces for the manipulation of the 3D objects within the framework. Common software programming language bindings for rendering frameworks include but are not limited to C++, Java, and C#. Additionally, the application software can provide settings to allow a test administrator to adjust actions within the test, such as holographic object speed and object color.

The system 100 can be configured to perform a variety of eyes tests, including, but not limited to, acuity testing (near and far), phorias, horizontal divergence, horizontal convergence, and refraction.

Figure 2:
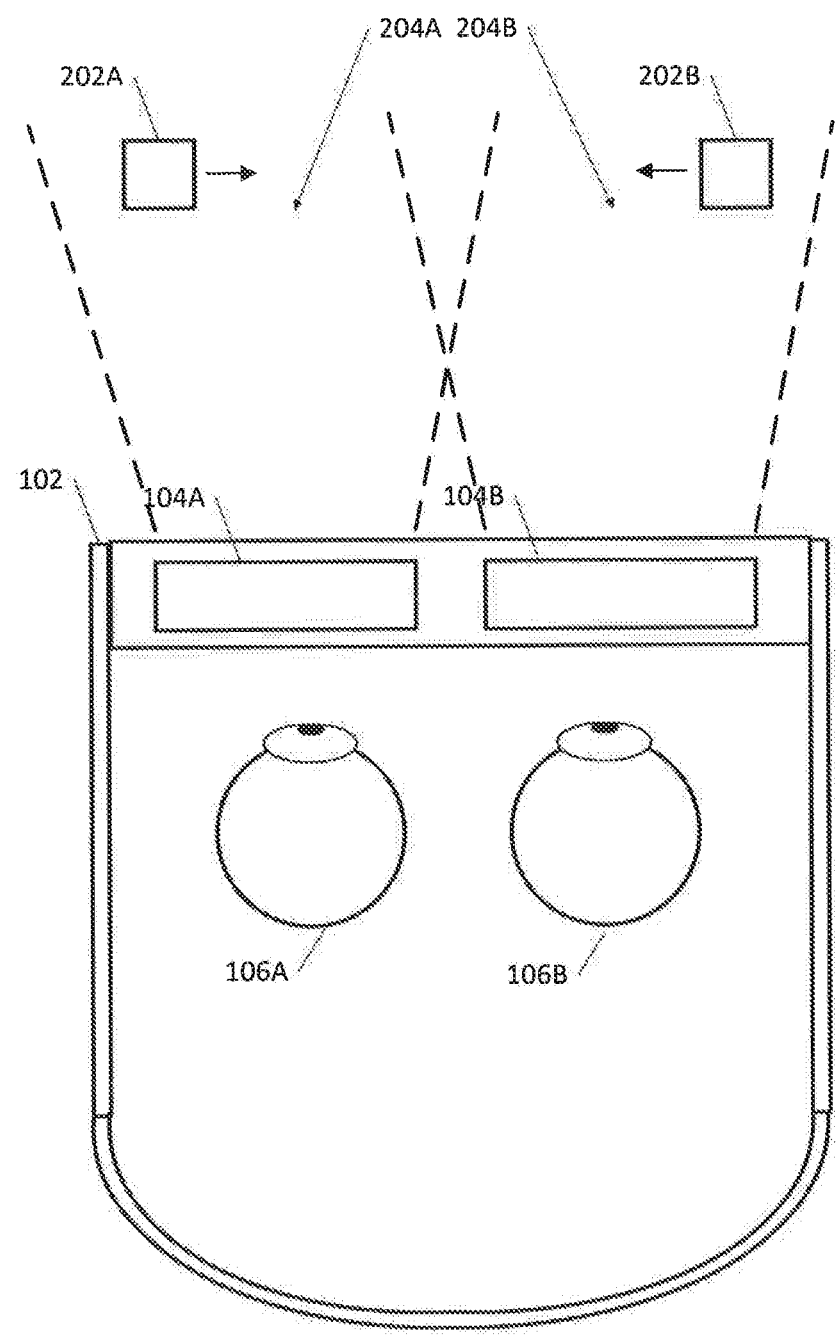
FIG. 2 is a block diagram illustrating a test for horizontal phoria with a holographic eye testing device according to an exemplary embodiment.

FIG. 2 is a block diagram illustrating a test for horizontal phoria with a holographic eye testing device according to an exemplary embodiment. In one embodiment, two virtual 3D objects 202A, 202B can be manipulated in a user's field of view (FOV) 204A, 204B. The virtual 3D objects 202A, 202B can be translated within the same horizontal plane until convergence. The virtual 3D objects 202A, 202B can have a starting point within the user's FOV 204A, 204B equidistant within the same horizontal plane from a midpoint of the FOV. Utilizing application software, the virtual 3D objects 202A, 202B are translated and projected on the combiner lenses 104A, 104B to give the appearance that the virtual 3D objects are a set distance from the view of the user's eyes 106A, 106B. The application software can present the virtual 3D objects 202A, 202B via the combiner lenses 104A, 104B so that the virtual 3D objects can appear to be at different distances from the user's eyes 106A, 106B. In some embodiments, the presentation of the virtual 3D objects 202A, 202B can correspond to projection of the virtual 3D objects at distances of 16 inches to 20 feet in front of the user's eyes 106A, 106B. The range of distances allow phoria to be measured at different intervals of depth for better confidence in convergence results. As the virtual 3D objects 202A, 202B approach the mid-point of the user's FOV, the user can provide input to the application software or platform software. The input can take the form of voice commands, gestures, or input from a "clicker." As the virtual 3D objects 202A, 202B approach each other, they will begin to overlap and converge into a single virtual 3D object. At the point in which the convergence becomes clear to the user, the user can provide input to stop any motion or translation of the virtual 3D objects 202A, 202B. The application software evaluates a delta between the midpoint of the user's FOV 204A, 204B and the point at which the virtual 3D objects 202A, 202B were located when the user provided input to stop the motion or translation. The delta can be represented as a deviation relative to the virtual distance of the virtual 3D objects 202A, 202B from the patient. A diopter is measured by the deviation of the image at a specific virtual distance (1 prism diopter=1 virtual cm deviation of the image at a 1 virtual meter distance).

Figure 3:
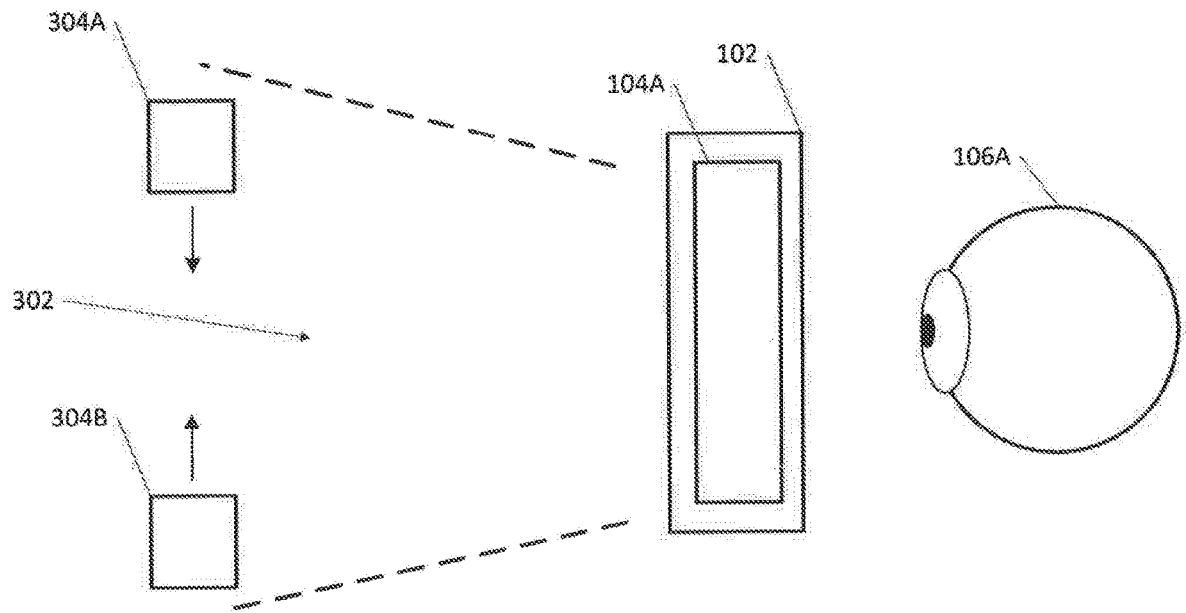
FIG. 3 is a block diagram illustrating a test for vertical phoria utilizing the holographic eye testing device according to an exemplary embodiment.

FIG. 3 is a block diagram illustrating a test for vertical phoria utilizing the holographic eye testing device according to an exemplary embodiment. In one embodiment, two virtual 3D objects 304A, 304B can be manipulated in a user's FOV 302. The virtual 3D objects 304A, 304B can be translated within the same vertical plane until convergence. The virtual 3D objects 304A, 304B can have a starting point within the user's FOV 302 equidistant within the same vertical plane from a mid-point of the FOV. Utilizing application software, the virtual 3D objects 304A, 304B are translated and projected on the combiner lenses 104A, 104B to give the appearance that the virtual 3D objects are a set distance from the view of the user's eyes 106A, 106B. The application software can present the virtual 3D objects 304A, 304B via the combiner lenses 104A, 104B so that the virtual 3D objects can appear to be at different distances from the user's eyes 106A, 106B. In some embodiments, the presentation of the virtual 3D objects 304A, 304B can correspond to projection of the virtual 3D objects at distances of 16 inches to 20 feet in front of the user's eyes 106A, 106B. The range of distances allow phoria to be measured at different intervals of depth for better confidence in convergence results. As the virtual 3D objects 304A, 304B approach the mid-point of the user's FOV 302, the user can provide input to the application software or platform software. The input can take the form of voice commands, gestures, or input from a "clicker." As the virtual 3D objects 304A, 304B approach each other, they will begin to overlap and converge into a single visible virtual 3D object. At the point in which the convergence becomes clear to the user, the user can provide input to stop any motion or translation of the virtual 3D objects 304A, 304B. The application software evaluates a delta between the midpoint of the user's FOV 302 and the point at which the virtual 3D objects 304A, 304B were located when the user provided input to stop the motion or translation. As mentioned above, the delta can be represented as a deviation relative to the virtual distance of the virtual 3D objects 304A, 304B from the patient. A diopter is measured by the deviation of the image at a specific virtual distance (1 prism diopter=1 virtual centimeter deviation of the image at a 1 virtual meter distance).

Figure 4A:
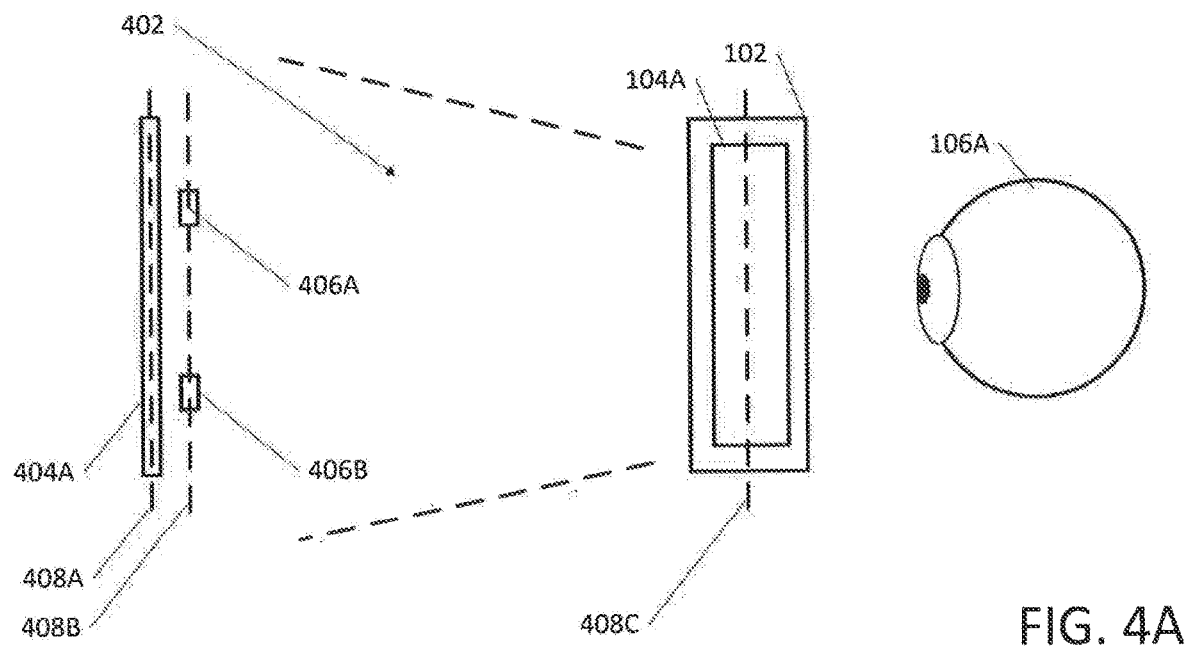
FIG. 4A is a block diagram illustrating a test for astigmatism utilizing the holographic eye testing device according to an exemplary embodiment.

FIG. 4A is a block diagram illustrating a test for astigmatism utilizing the holographic eye testing device according to an exemplary embodiment. In one embodiment, multiple virtual 3D objects 404A, 406A, 406B can be manipulated in a user's FOV 402. The virtual 3D objects 404A, 406A, 406B start in different planes 408A, 408B parallel to the plane of the combiner lenses 408C. In one embodiment, the virtual 3D objects 404A can be a set of vertical lines (relative to the user's eyes 106A, 106B) residing in a plane 408A. Additional virtual 3D objects 406A, 406B can be a set of horizontal lines (relative to the user's eyes 106A, 106B) residing in a plane 408B. When viewed through the combiner lenses 104A, 104B in the FOV 402, the virtual 3D objects 404A, 406A, 406B can appear as a hash mark (#) where the virtual 3D objects appear to intersect, however since they are in different planes 408A, 408B they do not actually intersect.

In one embodiment, the user can start the test by providing input to the computing system 108. The input can take the form of voice commands, including saying key words indicative of beginning the test, gestures or providing input from a "clicker." In one embodiment, the user states the word "start" to begin the test. Control of the test can take the form voice commands including "forward" and "backward." A voice command of "forward" translates the plane 408A, and associated virtual 3D objects 404A toward the combiner lenses 104A, 104B. A voice command of "backward" translates the plane 408A, and associated virtual 3D objects 404A away from the combiner lenses 104A, 104B. Utilizing the voice commands and associated translations, a user can manipulated the virtual 3D objects 404A where the user believes the respective planes 408A, 408B and associated virtual 3D objects 404A, 406A, 406B are coincidental. The user can provide a voice command to the computing system 108, such as stating the word "stop" to complete the manipulation portion of the test. Upon the receipt of the "stop" command, the computing system 108 disallows subsequent input commands, such as "forward" and "backward," and determines a delta distance between the final location of the planes 408A, 408B. In the event the user manipulated the planes 408A, 408B to coincide, the delta would be zero.

Figure 4B:
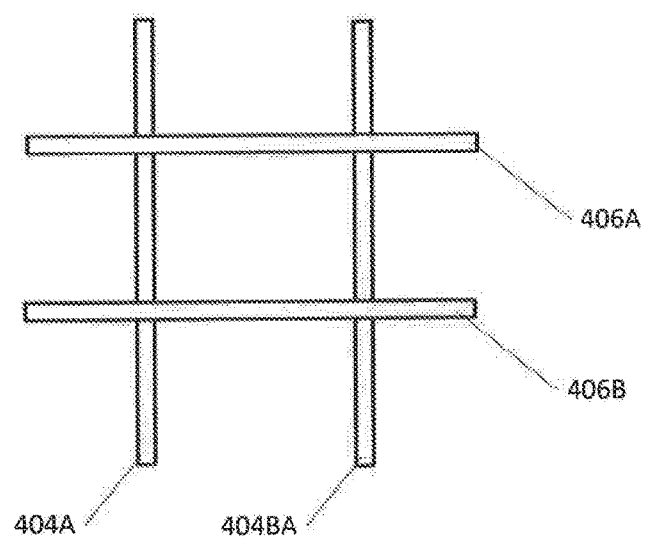
FIG. 4B is a block diagram illustrating a user's perspective of the virtual 3D objects depicted in FIG. 4A according to an exemplary embodiment.

FIG. 4B is a block diagram illustrating a user's perspective of the virtual 3D objects depicted in FIG. 4A. Virtual 3D objects 406A, 406B can be implemented as parallel lines residing the same plane 408B. Virtual 3D objects 404A, 404B can be implemented as parallel lines residing in the same plane 408A.

Figure 5A:
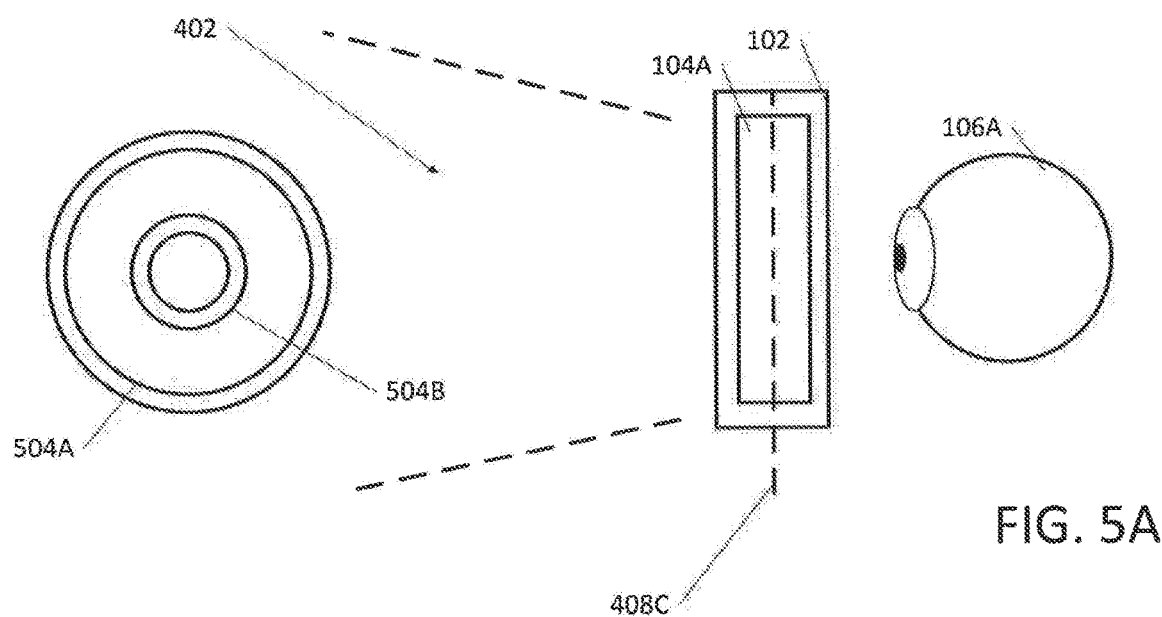
FIG. 5A is a block diagram illustrating a test for astigmatism utilizing the holographic eye testing device according to an exemplary embodiment.
Figure 5B:
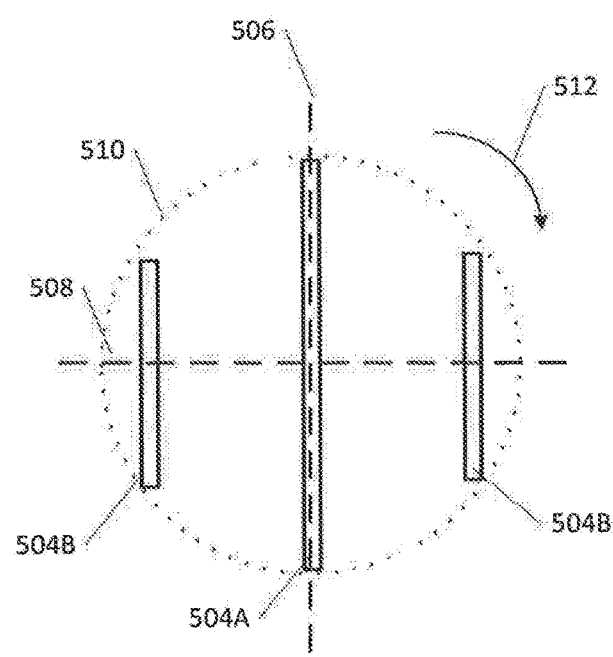
FIG. 5B is a block diagram illustrating a user's perspective of the virtual 3D objects depicted in FIG. 5A according to an exemplary embodiment.

FIG. 5A is a block diagram illustrating a test for astigmatism utilizing the holographic eye testing device according to an exemplary embodiment. FIG. 5B is a block diagram illustrating a user's perspective of the virtual 3D objects depicted in FIG. 5A. In one embodiment, multiple virtual 3D objects 504A, 504B can be manipulated in a user's FOV 402. The virtual 3D objects 504A, 504B correspond to concentric opaque rings across the surface of an invisible sphere 510, where the concentric opaque rings traverse the surface of the sphere perpendicular to the plane of the combiner lenses 104A, 104B. The virtual 3D objects 504A, 504B can be oriented along coaxial planes 506, 508. In other embodiments, the virtual 3D objects 504A, 504B can be distal or proximal portions of concentric opaque rings across the surface of an invisible sphere 510.

In one embodiment, the user can start the test by providing input to the computing system 108. The input can take the form of voice commands, including saying key words indicative of beginning the test, gestures or providing input from a "clicker." The user states the word "start" to begin the test. As the test begins, the invisible sphere 510 and accompanying virtual 3D objects are translated toward the combiner lenses 104A, 104B to give the user the appearance that the virtual 3D objects are coming directly at the user's eyes 106A. When the user can see the virtual 3D objects 504A, 504B clearly, the user can provide input to stop the test in the form of a voice command of "stop." The computing system 108 ceases translation of the invisible sphere 510 and calculates a delta distance from the starting point of the invisible sphere to the point where the invisible sphere resides at the end of the test. A constant point of reference on the invisible sphere 510 can be utilized to determine a consistent location to determine the delta distance.

In another embodiment, the user can start the test by providing input to the computing system 108. The input can take the form of voice commands, including saying key words indicative of beginning the test, gestures or providing input from a "clicker." The user states the word "start" to begin the test. The virtual 3D objects 504A, 504B being the test in a parallel or coincidental plane with a starting plane 506. As the test begins the invisible sphere 510 and accompanying virtual 3D objects are rotated in a clockwise motion 512 from the user's perspective. When the invisible sphere 510 and accompanying virtual 3D objects appear to have rotated ninety (90) degrees from the original starting position, (parallel or coincidental to the horizontal plane 508), the user can provide input to stop the test in the form of a voice command of "stop." The computing system 108 ceases rotation of the invisible sphere 510 and calculates a delta in degrees based on the rotation from the starting point of the invisible sphere to the orientation of the invisible sphere at the end of the test. The delta in degrees can be used to determine the axis of the astigmatism. This provides the amount of astigmatism measured in this eye and therefore the predicted amount of cylindrical correction needed to bring clarity.

Figure 5C:
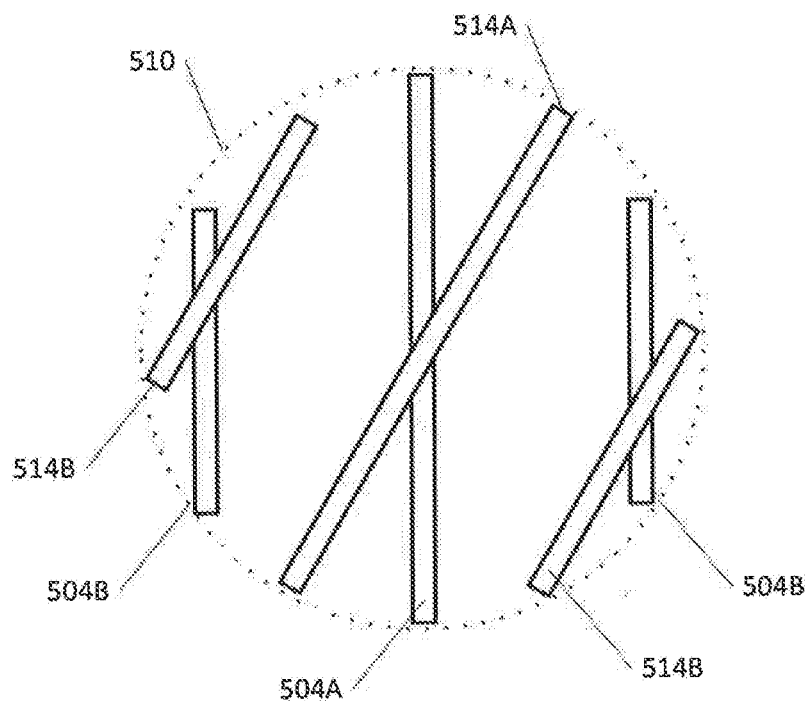
FIG. 5C is a block diagram illustrating another perspective of the virtual 3D objects depicted in FIG. 5A according to an exemplary embodiment.

FIG. 5C is a block diagram illustrating another user's perspective of the virtual 3D objects depicted in FIG. 5A. In another embodiment, the virtual 3D objects 504A, 504B can be distal portions of concentric opaque rings across the surface of an invisible sphere 510. The virtual 3D objects 514A, 514B can be proximal portions of concentric opaque rings across the surface of an invisible sphere 510. The distal portions of the concentric opaque rings form a group and the proximal portions form a group. Groups are rotated and translated in the FOV 402 in unison. The distal portions can be offset from the proximal portions by a rotation of 45 degrees. The user can start the test by providing input to the computing system 108. The input can take the form of voice commands, including saying key words indicative of beginning the test, gestures or providing input from a "clicker." The user states the word "start" to begin the test. The computing system 108 translates virtual 3D objects 514A, 514B corresponding to the proximal portions toward the combiner lenses 104A, 104B where the virtual 3D object 514A, 514B appear to be coming toward the user's eyes 102A, 102B. When the user determines that the virtual 3D objects 514A, 514B are clear and distinct from the distal virtual 3D objects 504A, 504B, the user can provide input to stop the test in the form of a voice command of "stop." The computing system 108 ceases translation of the virtual 3D objects 514A, 514B corresponding to the proximal portions and calculates a delta in distance based on the translation from the starting point to the position at the end of the test.

Figure 6A:
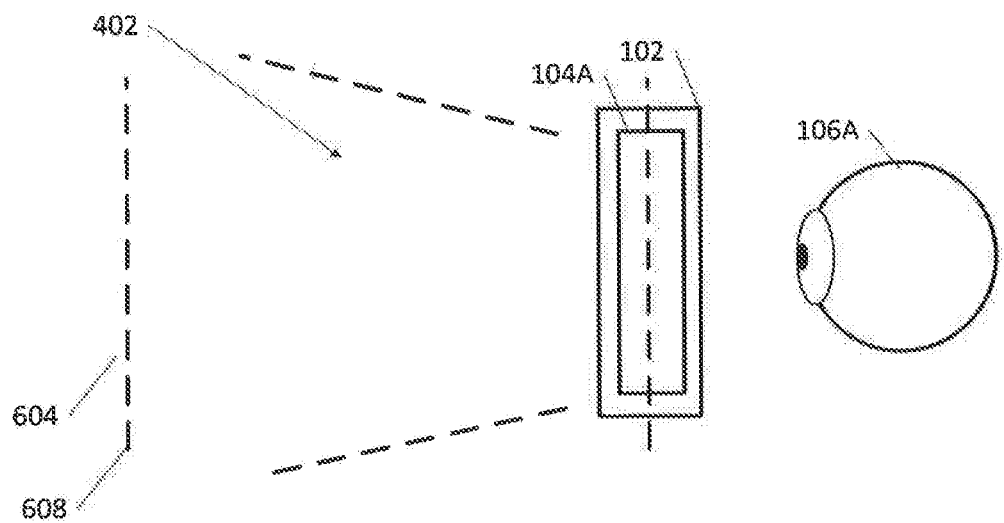
FIGS. 6A-6B are diagrams illustrating a test for visual acuity utilizing the holographic eye testing device according to an exemplary embodiment.

FIG. 6A is a block diagram illustrating a test for visual acuity utilizing the holographic eye testing device, according to an exemplary embodiment. In one embodiment, virtual 2D or 3D letters or images 604 can be displayed and/or manipulated in a user's FOV 402. Utilizing application software, the virtual letters or images 604 are translated and projected on the combiner lenses 104A, 104B to give the appearance that the virtual letters or images 604 are a set distance from the view of the user's eyes 106A, 106B. The application software can present the virtual letters or images 604 via the combiner lenses 104A, 104B so that the virtual letters or images 604 can appear to be at different distances from the user's eyes 106A, 106B. In some embodiments, the presentation of the virtual letters or images 604 can correspond to projection of the virtual letters or images 604 at distances of 16 inches (near visual acuity) to 20 feet (distance visual acuity) in front of the user's eyes 106A, 106B. The visual acuity test is used to determine the smallest letters or images a user can identify from the virtual letters or images 604 at a specified distance away (e.g., 6 meters). The range of distances allows visual acuity to be measured at different intervals of depth.

In one embodiment, the user can start the test by providing input to the computing system 108. The input can take the form of voice commands, including saying key words indicative of beginning the test, gestures or providing input from a "clicker." In one embodiment, the user states the word "start" to begin the test.

In some embodiments, the virtual letters or images 604 can be moved forward or backwards. Control of the test can take the form voice commands including "forward" and "backward." A voice command of "forward" translates the plane 608, and associated virtual letters or images 604 toward the combiner lenses 104A, 104B. A voice command of "backward" translates the plane 608, and associated virtual letters or images 604 away from the combiner lenses 104A, 104B. Utilizing the voice commands and associated translations, a user can manipulated the virtual letters or images 604 until the user can or can no longer identify the virtual letters or images 604. The user can provide a voice command to the computing system 108, such as stating the word "stop" to complete the manipulation portion of the test. Upon the receipt of the "stop" command, the computing system 108 disallows subsequent input commands, such as "forward" and "backward," and determines a final distance of the virtual letters or images 604B.

Figure 6B:
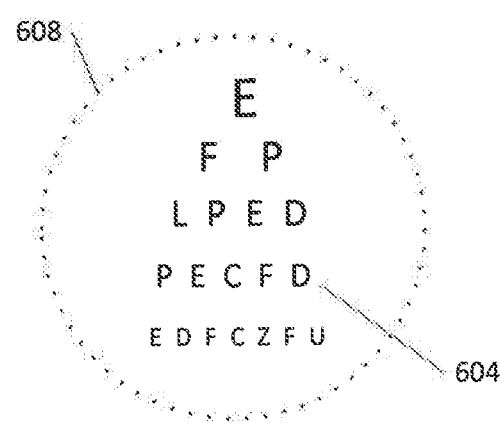

FIG. 6B is a block diagram illustrating a user's perspective of the virtual letters depicted in FIG. 6A. The virtual letters 604 can be implemented as letters residing on the same plane 608. In other embodiments, one or more of the virtual letters 604 can be implemented as letters residing on different planes.

Figure 7A:
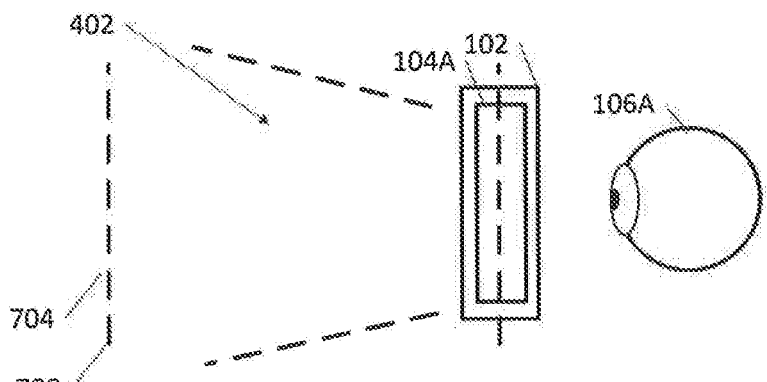
FIGS. 7A-7G are diagrams illustrating tests for horizontal convergent and horizontal divergent, utilizing the holographic eye testing device according to an exemplary embodiment.

FIG. 7A is a block diagram illustrating a test for horizontal convergent and horizontal divergent, utilizing the holographic eye testing device according to an exemplary embodiment. In one embodiment, virtual 2D or 3D shapes 704 can be displayed and/or manipulated in a user's FOV 402. The horizontal convergent and horizontal divergent tests are used to examine eye movement responses to symmetric stimuli.

In one embodiment, the virtual shapes 704 can be manipulated in a user's field of view (FOV) 402. The virtual shapes 704 can have a starting point within the user's FOV 402 equidistant within the same horizontal plane from a midpoint of the FOV 402. Utilizing application software, the virtual shapes 704 are translated and projected on the combiner lenses 104A, 104B to give the appearance that the virtual shapes 704 are a set distance from the view of the user's eyes 106A, 106B. The application software can present the virtual shapes 704 via the combiner lenses 104A, 104B so that the virtual shapes 704 can appear to be at different distances from the user's eyes 106A, 106B. In some embodiments, the presentation of the virtual shapes 704 can correspond to projection of the virtual shapes 704 at distances of 16 inches to 20 feet in front of the user's eyes 106A, 106B. The range of distances allows the horizontal convergent and the horizontal divergent to be measured at different intervals of depth for better confidence in convergence and divergence results.

In one embodiment, the user can start the test by providing input to the computing system 108. The input can take the form of voice commands, including saying key words indicative of beginning the test, gestures or providing input from a "clicker." In one embodiment, the user states the word "start" to begin the test.

Figure 7B:
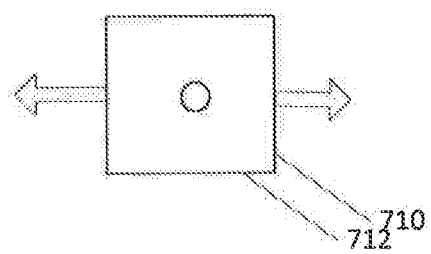
Figure 7C:
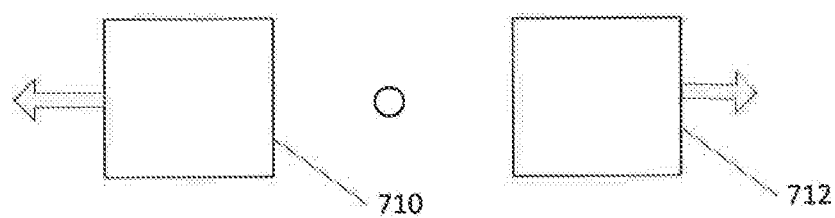

FIGS. 7B-7C are block diagrams illustrating a horizontal convergent test, utilizing the holographic eye testing device according to an exemplary embodiment.

The horizontal convergent test is performed in two stages—a break stage and a recovery stage. Two objects (for example, 3D or 2D shapes, such as 3D cubes) are presented to a user at a given distance. The distance can be changed depending on needs of the user, such as whether the test is being performed for near-sightedness or far-sightedness. A first object 710 of the two objects is projected to a right eye and a second object 712 of the two objects is projected to the left eye.

For the break stage of the test, the first object 710 and the second object 712 begin overlaid on each other and appear as one object, as shown in FIG. 7B. The first object 710 and the second object 712 slowly move apart. The first object 710 shown to the right eye moves to the left from a center start point, and the second object 712 shown to the left eye moves to the right from the center start point, as shown in FIG. 7C. The user reports when the user notices that instead of viewing the single object, the user now views that there are two objects (the first object 710 and the second object 712).

During the break stage, as the first object 710 and the second object 712 move from the center start point of the user's FOV 402, the user can provide input to the application software or platform software. The input can take the form of voice commands, gestures, or input from a "clicker." As the first object 710 moves to the left from the center start point and the second object 712 moves to the right from the center start point, the objects will begin to diverge and appear as separate objects. At the point in which the divergence becomes clear to the user, the user can provide input to stop any motion or translation of the first object 710 and the second object 712. The application software evaluates a delta between the midpoint of the user's FOV 402 and the point at which the first object 710 and the second object 712 were located when the user provided input to stop the motion or translation. The delta can be represented as a deviation relative to the virtual distance of the first object 710 and the second object 712 from the user. A diopter is measured by the deviation of the object at a specific virtual distance (1 prism diopter=1 virtual cm deviation of the object at a 1 virtual meter distance).

Figure 7D:
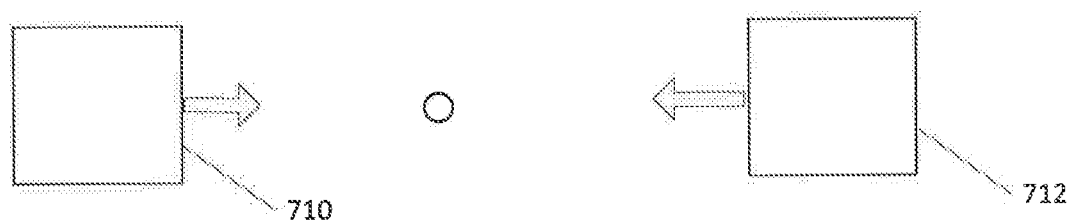

For the recovery stage of the test, the first object 710 and the second object 712 start out offset from each other and slowly move together. The first object 710 shown to the right eye starts on the left side of the user's view and moves to the center start point, and the second object 712 shown to the left eye starts on the right side of the user's view and moves to the center start point, as shown in FIG. 7D. The user reports when the user no longer views two distinct objects, but instead only a single object.

During the recovery stage, as the first object 710 and the second object 712 approach the center start point of the user's FOV 402, the user can provide input to the application software or platform software. The input can take the form of voice commands, gestures, or input from a "clicker." As the first object 710 and the second object 712 approach each other, they will begin to overlap and converge into a single object. At the point in which the convergence becomes clear to the user, the user can provide input to stop any motion or translation of the first object 710 and the second object 712. The application software evaluates a delta between the midpoint of the user's FOV 402 and the point at which the first object 710 and the second object 712 were located when the user provided input to stop the motion or translation. The delta can be represented as a deviation relative to the virtual distance of the first object 710 and the second object 712 from the user. A diopter is measured by the deviation of the object at a specific virtual distance (1 prism diopter=1 virtual cm deviation of the object at a 1 virtual meter distance).

Figure 7E:
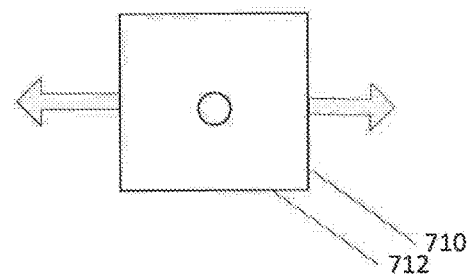
Figure 7F:
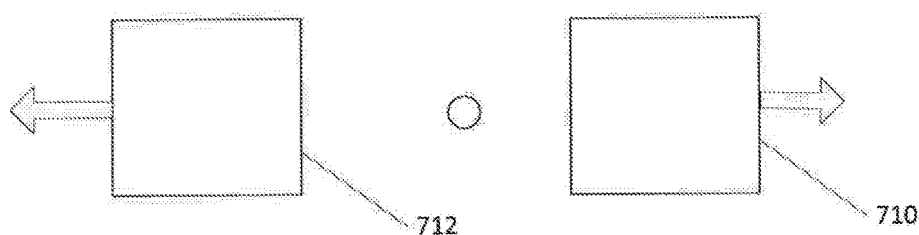
Figure 7G:
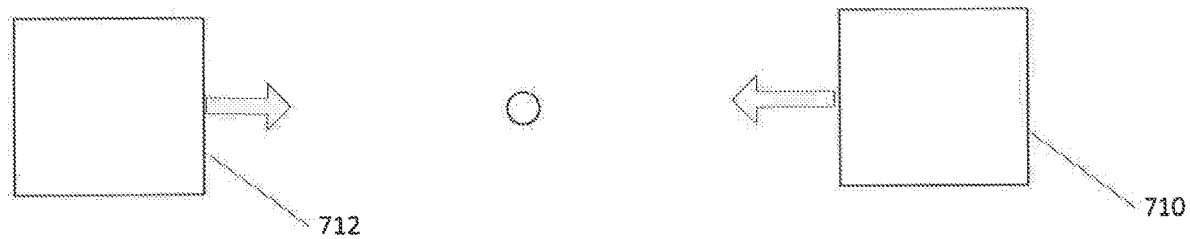

FIGS. 7E-7G is a block diagram illustrating a horizontal divergent test, utilizing the holographic eye testing device according to an exemplary embodiment.

The horizontal divergent is performed in two stages—a break stage and a recovery stage. Two objects (for example, 3D or 2D shapes, such as 3D cubes) are presented to a user at a given distance. The distance can be changed depending on needs of the user, such as whether the test is being performed for near-sightedness or far-sightedness. A first object of the two objects is projected to a right eye and a second object of the two objects is projected to the left eye.

The difference between horizontal divergent test and the horizontal convergent tests has to do with what object is shown to what eye, and where the objects move. For divergent test, the objects are shown to the opposite eye from the convergent test.

For the break stage of the test, the first object 710 and the second object 712 begin overlaid on each other and appear as one object, as shown in FIG. 7E. The first object 710 and the second object 712 slowly move apart. The first object 710 shown to the right eye moves to the right from the center start point, and the second object 712 shown to the left eye moves to the left from the center start point, as shown in FIG. 7F. The user reports when the user notices that instead of viewing the single object, the user now views that there are two objects (the first object 710 and the second object 712).

During the break stage, the first object 710 and the second object 712 move from the center start point of the user's FOV 402, the user can provide input to the application software or platform software. The input can take the form of voice commands, gestures, or input from a "clicker." As the first object 710 moves to the right from the center start point and the second object 712 moves to the left from the center start point, the objects will begin to diverge and appear as separate objects. At the point in which the divergence becomes clear to the user, the user can provide input to stop any motion or translation of the first object 710 and the second object 712. The application software evaluates a delta between the midpoint of the user's FOV 402 and the point at which the first object 710 and the second object 712 were located when the user provided input to stop the motion or translation. The delta can be represented as a deviation relative to the virtual distance of the first object 710 and the second object 712 from the user. A diopter is measured by the deviation of the object at a specific virtual distance (1 prism diopter=1 virtual cm deviation of the object at a 1 virtual meter distance).

For the recovery stage of the test, the first object 710 and the second object 712 start out offset from each other and slowly move together, as shown in FIG. 7G. The first object 710 shown to the right eye starts on the right side of the user's view and moves to the center start point, and the second object 712 shown to the left eye start's on the left side of the user's view and moves to the center start point. The user reports when the user no longer views two distinct objects, but instead only a single object.

During the recovery stage, as the first object 710 and the second object 712 approach the center start point of the user's FOV 402, the user can provide input to the application software or platform software. The input can take the form of voice commands, gestures, or input from a "clicker." As the first object 710 and the second object 712 approach each other, the objects will begin to overlap and converge into a single object. At the point in which the convergence becomes clear to the user, the user can provide input to stop any motion or translation of the first object 710 and the second object 712. The application software evaluates a delta between the midpoint of the user's FOV 402 and the point at which the first object 710 and the second object 712 were located when the user provided input to stop the motion or translation. The delta can be represented as a deviation relative to the virtual distance of the first object 710 and the second object 712 from the user. A diopter is measured by the deviation of the object at a specific virtual distance (1 prism diopter=1 virtual cm deviation of the object at a 1 virtual meter distance).

For both the convergent test and the divergent test described above, the first object 710 is only shown the right eye and the second object 712 is only shown to the left eye. This means at the start of the convergent test and/or the divergent test, a user will see two objects, but if the user closes one eye, only one object will be visible to the user (the one object projected for that eye). This is how a fusion effect is achieved, where two objects suddenly appear to be one, at the start of the divergent test and at the end of the convergent test.

In the above convergent test and/or the divergent test, and along with most of the other tests, eye tracking data is important because it allows the system to determine where the user is looking. For these tests, along with others, the program may request that the user look at a certain point in order to start the test, or to confirm that they are looking in the right location and see the shapes before the test is started. For the phorias testing, the system may request that a user attempt to gaze at a certain point while the shapes are in motion in order to ensure that the tests return accurate results. If they look away from the point, or directly at the shapes, the test may pause and wait for them to return their gaze to the requested object before continuing.

Figure 8A:
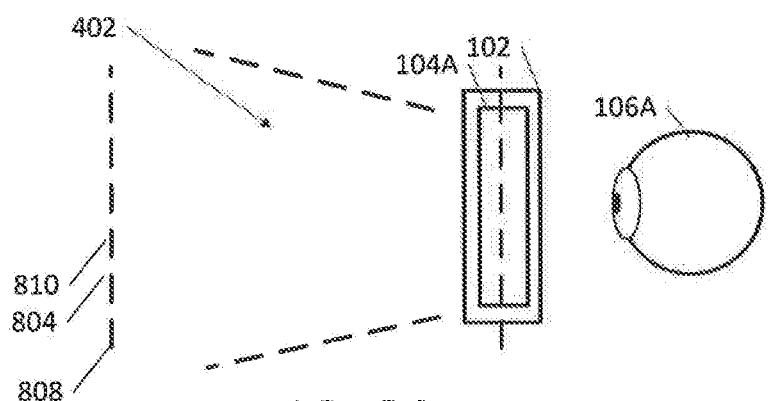
FIGS. 8A-8C are diagrams illustrating refraction testing utilizing the holographic eye testing device according to an exemplary embodiment.
Figure 8B:
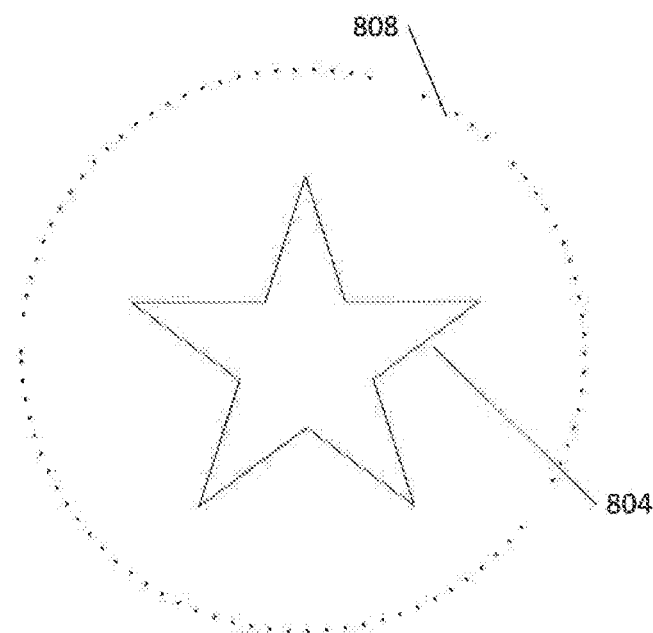
Figure 8C:
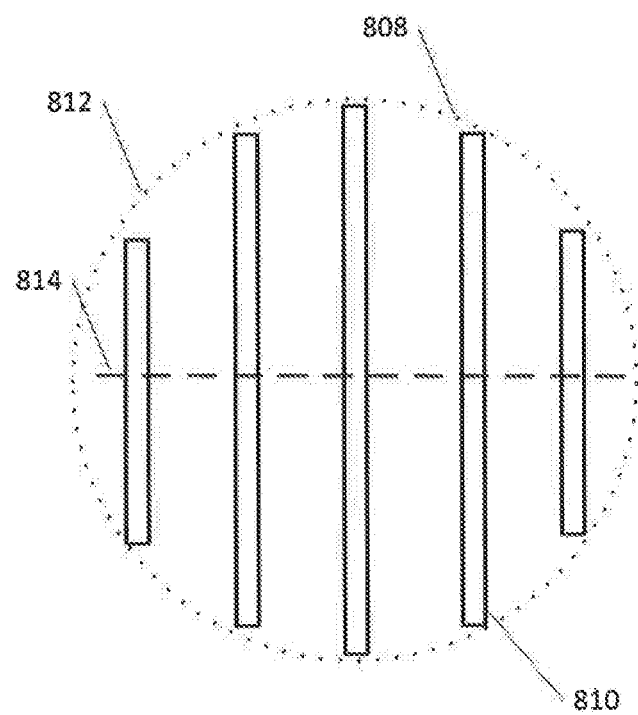

FIGS. 8A-8C are diagrams illustrating refraction testing utilizing the holographic eye testing device according to an exemplary embodiment. As shown in FIG. 8A, in one embodiment, at least one virtual object 804 and/or a series of virtual lines 810 can be displayed and/or manipulated in a user's FOV 402. Utilizing application software, the object 804 or the series of lines 810 are translated on a vertical plane 808 and projected on the combiner lenses 104A, 104B to give the appearance that the object 804 or the series of lines 810 is a set distance from the view of the user's eyes 106A, 106B. The application software can present the object 804 or the series of lines 810 via the combiner lenses 104A, 104B so that the object 804 or the series of lines 810 can appear to be at different distances from the user's eyes 106A, 106B. In some embodiments, the presentation of the object 804 or the series of lines 810 can correspond to projection of virtual letters, images, or lines at distances of 16 inches (near visual acuity) to 20 feet (distance visual acuity) in front of the user's eyes 106A, 106B.

In one embodiment, the user can start the test by providing input to the computing system 108. The input can take the form of voice commands, including saying key words indicative of beginning the test, gestures, or providing input from a "clicker." In one embodiment, the user states the word "start" to begin the test.

The described systems and methods use depth of field for testing refraction. The refraction testing determines the user's level of hyperopia (farsightedness), myopia (nearsightedness), and astigmatism, and three associated numerical values for sphere, cylinder, and axis, typically needed for an eyeglass prescription.

In the first step, the computing system 108 measures the refractive state of the eye by having the user move the object 804 from an initial distance towards or away from the user until a resolution of the object 804 appears clear to the user. The distance at which the object 804 appears clear to the user is labeled as a final distance. The computing system 108 determines an initial measurement between the final position of the virtual object and an optimal virtual position. This initial measurement is at the focal length of the refractive spherical equivalent of the eye and is the sphere power. The sphere power indicates the amount of lens power, measured in diopters (D), prescribed to correct nearsightedness or farsightedness.

In the second step, a series of virtual lines 810 are presented at the final distance in a parallel or coincidental plane with the plane 808. In a first embodiment, the series of lines 810 correspond to concentric opaque rings across the surface of an invisible sphere 812 (shown in FIG. 8C), where the concentric opaque rings traverse the surface of the sphere 812 perpendicular to the plane of the combiner lenses 104A, 104B. In a second embodiment, the series of lines 810 includes a predefined number of lines (for example, three lines) in the axis plane.

In the first embodiment, as the test begins, the invisible sphere 812 and accompanying series of lines 810 are rotated in a clockwise motion from the user's perspective. When the invisible sphere 812 and accompanying series of lines 810 appear to have rotated ninety (90) degrees about an axis from the final position, (parallel or coincidental to the axis 814 shown in FIG. 8C), the user can provide input to stop the test, for example, in the form of a voice command of "stop." The computing system 108 ceases rotation of the invisible sphere 812 and calculates a delta in degrees based on the rotation from the starting point of the invisible sphere 812 to the orientation of the invisible sphere 812 at the end of the test. The delta in degrees can be used to determine the axis value.

The second step provides the axis. This provides the amount of astigmatism measured in this eye and therefore the predicted amount of cylindrical correction needed to bring clarity. The cylinder value refers to the amount of astigmatism in the eyes.

In the third step, the lines 810 are shifted 90 degrees from the axis 814 and moved further away from the user to display a blurred side of the lines 810. The user moves the lines 810 closer to or farther from (plus cylinder or minus cylinder) the user until the lines appear clear to the user. This is the focal length of the cylinder power and corresponds to the difference in power from the sphere.

Based on the above, the sphere, cylinder, and axis values are determined. The above described sequence provides the amount of hyperopia (farsightedness), myopia (nearsightedness), and astigmatism measured in this eye and therefore the predicted amount of correction needed to bring clarity. If the user has both myopia or hyperopia and astigmatism, the object 804 would be simultaneously manipulated to determine myopia or hyperopia while also evaluation the dioptric power of the astigmatism.

In some embodiments, when measuring hyperopia, plus (convex) lenses are included in the HMD 102 underneath the lenses 104A, 104B and in front of the user's eyes 106A, 106B. The reason for this is that the hyperopic eye focuses beyond the fixation object. In order to measure the hyperopia, the hyperopic eye is mathematically made to become myopic An algorithm is used to subtracts the values to determine the dioptric value of the hyperopis.

In some embodiments, a fourth step is included to refine the exact sphere power and then to binocularly balance the prescription for the two eyes. In the fourth step, the object 804 is shifted further away from the user to create +0.50 diopters in each the user's eyes 106A, 106B. The object 804 initially appears as one object to the user and then is disassociated or separated until the user can identify two separate objects. The user reports which object is clearer. The clearer object is then moved away from the user until both objects appear equally as blurred. The objects are then merged and the user moves them closer until the resolution appears best to the user. The binocular balance has then been completed.

The object 804 and lines 810 can be moved forward or backwards or rotated. Control of the test can take the form voice commands including "forward," "backward," and "rotate." A voice command of "forward" translates the plane 808, and associated object 804 or lines 810 toward the combiner lenses 104A, 104B. A voice command of "backward" translates the plane 808, and associated object 804 or lines 810 away from the combiner lenses 104A, 104B. A voice command of "rotate" moves the plane 808, and associated object 804 or lines 810 in a rotation manner Utilizing the voice commands and associated translations, a user can manipulate the object 804 until the user can or can no longer identify the object 804 or lines 810. The user can provide a voice command to the computing system 108, such as stating the word "stop" to complete the manipulation portion of the test.

FIG. 8B is a block diagram illustrating a user's perspective of the virtual object 804 described in FIG. 8A. The virtual object 804 can be implemented as one or more virtual 2D or 3D letters or images, such as shapes, pictures, etc., residing on the plane 808.

FIG. 8C is a block diagram illustrating a user's perspective of the series of lines 810 described in FIG. 8A. The series of lines 810 can be implemented as parallel lines (running vertical and/or horizontal) residing on the plane 808. The series of lines 810 correspond to concentric opaque rings across the surface of the invisible sphere 812, where the concentric opaque rings traverse the surface of the sphere 812 perpendicular to the plane of the combiner lenses 104A, 104B.

Figure 9A:
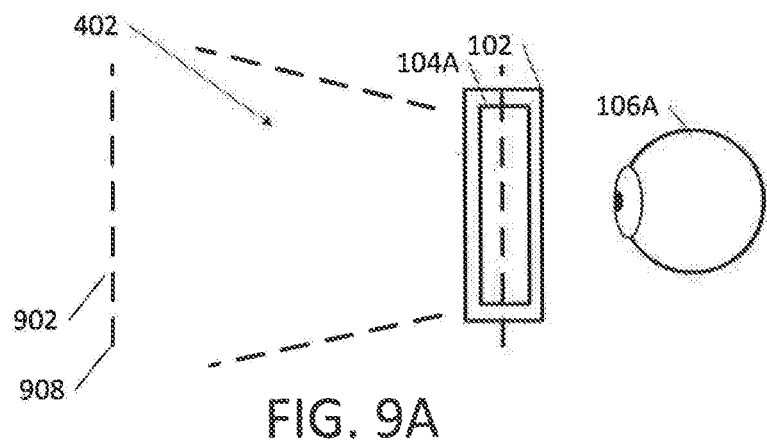
FIGS. 9A-9B are diagrams illustrating convergence testing utilizing the holographic eye testing device according to an exemplary embodiment.

FIG. 9 is a block diagram illustrating convergence testing utilizing the holographic eye testing device according to an exemplary embodiment. The head mounted display (HMD) 102 incorporates eye tracking. Eye tracking enables the HMD 102 to track where the user's eyes 106A, 106B are looking in real time. As shown in FIG. 9A, in one embodiment, at least one virtual object 902 can be displayed and/or manipulated in a user's FOV 402. Utilizing application software, the object 902 is translated on a vertical plane 908 and projected on the combiner lenses 104A, 104B to give the appearance that the object 902 is a set distance from the view of the user's eyes 106A, 106B. The application software can present the object 902 via the combiner lenses 104A, 104B so that the object 902 can appear to be at different distances from the user's eyes 106A, 106B. In some embodiments, the presentation of the object 902 can correspond to projection of virtual letters, images, or lines at distances of 16 inches (near visual acuity) to 20 feet (distance visual acuity) in front of the user's eyes 106A, 106B.

In one embodiment, the user can start the test by providing input to the computing system 108. The input can take the form of voice commands, including saying key words indicative of beginning the test, gestures, or providing input from a "clicker." In one embodiment, the user states the word "start" to begin the test.

During the convergence testing, the object 902 is presented to each eyes 106A, 106B and is moved across the user's FOV 402. The user follows the object 902 from left to right and right to left. The object 902 is then moved in a circle clock wise and counter-clockwise. The HMD 102, via eye tracking, monitors fixation loss and quality of movement of the user's eyes 106A, 106B. Points of fixation loss and the quality of movement are recorded.

Convergence near point will be assessed by rendering a first virtual object 910 displayed to a right eye and a second virtual object 912 displayed to a left eye within the holographic display device, wherein the rendering corresponds to the first virtual object and the second virtual object aligned to appear as one virtual object to the user. The first virtual object 910 and the second virtual object 912 appear at a distance of 40 centimeters in front of the user's eyes 106A, 106B. The user moves the first virtual object 910 and the second virtual object 912 presented to both eyes 106A, 106B toward the user's nose. The HMD 102 monitors eye alignment and record the distance (in centimeter or inches) when the eyes 106A, 106B lose alignment on the first virtual object 910 and the second virtual object 912 and the first virtual object 910 and the second virtual object 912 appears as two separate objects. This is recorded as the break point. The first virtual object 910 and the second virtual object 912 are then moved away from the user and the HMD 102 records the distance when the eyes 106A, 106B realign and the user fuses the first virtual object 910 and the second virtual object 912 back to appear as one virtual object to the user. This is recorded as the realignment point.

Figure 9B:
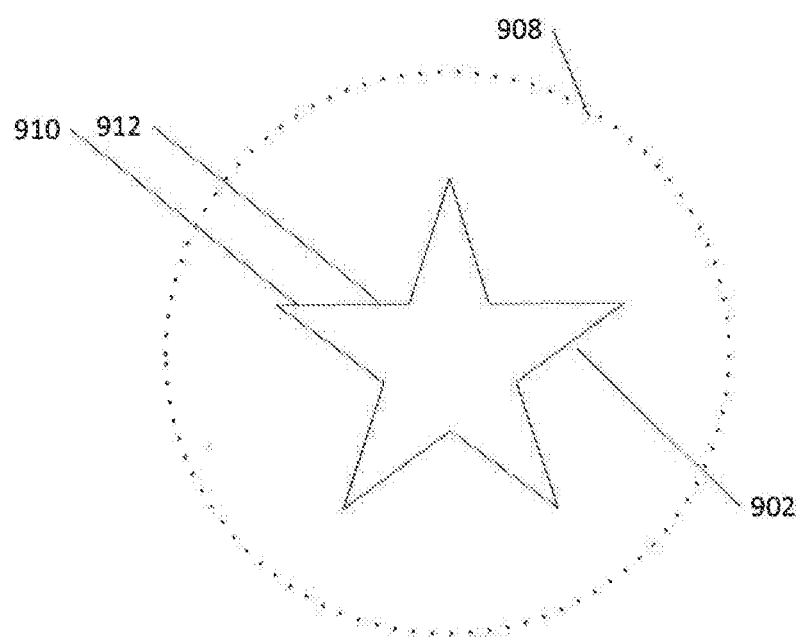

FIG. 9B is a block diagram illustrating a user's perspective of the virtual object 902 and/or the first virtual object 910 and the second virtual object 912 as viewed aligned, as described in FIG. 9A. The virtual object 804 can be implemented as one or more virtual 2D or 3D letters or images, such as shapes, pictures, etc., residing on the plane 908.

FIGS. 10A-10D illustrates methods for diagnosis and/or prescription of remedies for visual impairment in accordance with exemplary embodiments.

Figure 10A:
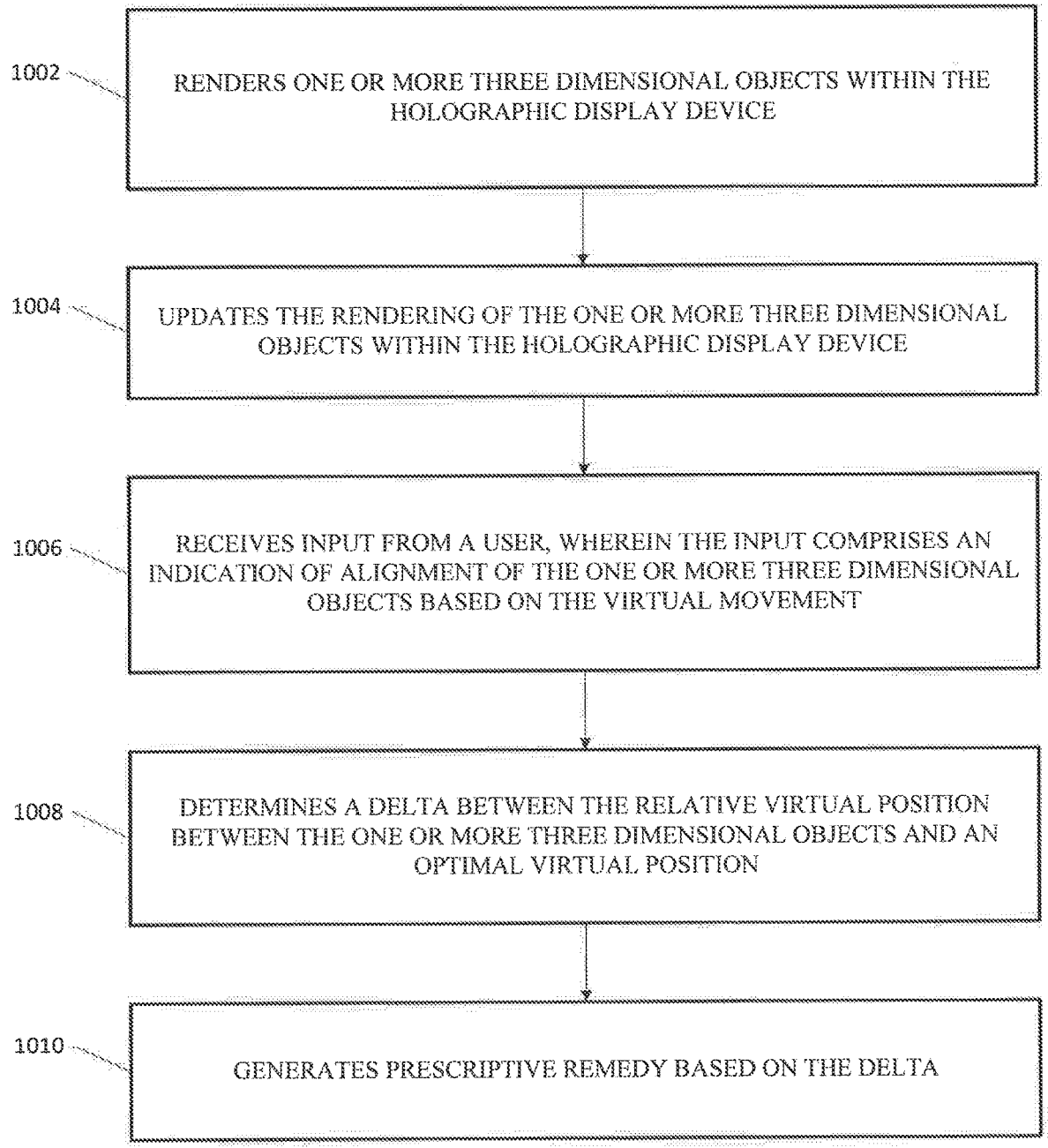
FIGS. 10A-10D are block diagrams illustrating methods for utilizing the holographic eye testing device according to an exemplary embodiment.

FIG. 10A illustrates a method for diagnosis and prescription of remedies for visual impairment in accordance with an exemplary embodiment.

At step 1002, the holographic display device renders one or more three dimensional objects with the holographic display device. The rendering corresponds to a virtual level of depth viewable by a user.

At step 1004, the holographic display device updates the rendering of the one or more three dimensional objects within the holographic display device. The updated rendering includes a virtual movement of the one or more three dimensional objects within the virtual level of depth. The virtual movement includes moving the one or more three dimensional objects laterally in the field of view of the user. Alternatively, the virtual movement includes moving the one or more three dimensional objects vertically in the field of view of the user. Additionally, the virtual movement includes moving the one or more three dimensional objects from a distal position to proximal position within the field of view of the user. The virtual level of depth corresponds to a simulated distance away from the user. The simulated distance can range from sixteen (16) inches to twenty (20) feet from the user.

At step 1006, the holographic display device receives input from a user. The input can include an indication of alignment of the one or more three dimensional objects based on the virtual movement. The indication of alignment can include a relative virtual position between the one or more three dimensional objects. The input from the user can include hand gestures and voice commands At step 1008, the holographic display device determines a delta between the relative virtual position of the one or more three dimensional objects and an optimal virtual position.

At step 1010, the holographic display device generates a prescriptive remedy based on the delta between the relative virtual position of the one or more three dimensional objects and the optimal virtual position.

Figure 10B:
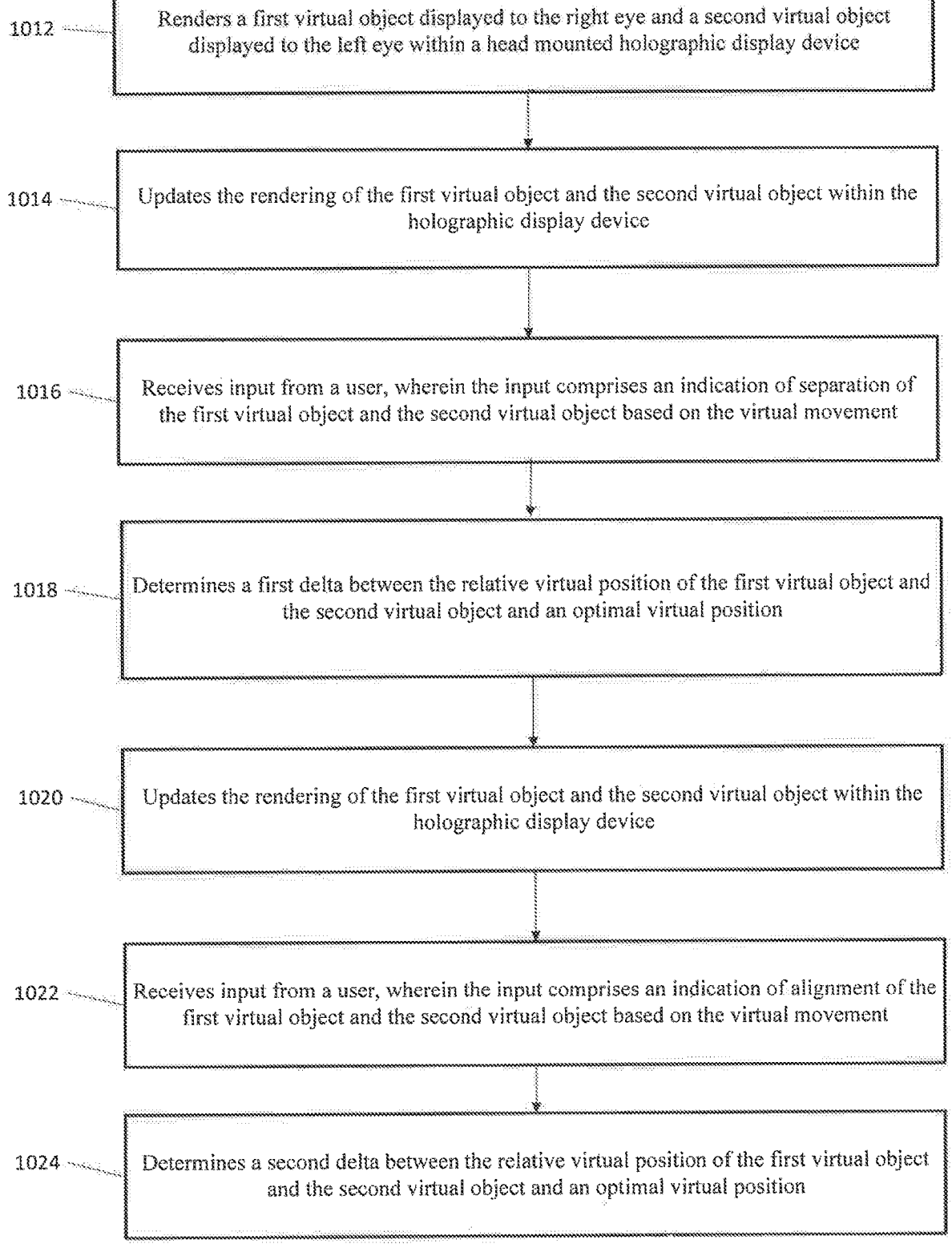

FIG. 10B illustrates a method for diagnosis and prescription of remedies for visual impairment in accordance with an exemplary embodiment.

At step 1012, a diagnostic module configured to execute on a computing device communicatively coupled to the head mounted holographic display device renders a first virtual object displayed to the right eye and a second virtual object displayed to the left eye within a head mounted holographic display device. The rendering corresponds to the first virtual object and the second virtual object aligned to appear as one virtual object to a user.

At step 1014, the diagnostic module updates the rendering of the first virtual object and the second virtual object within the holographic display device. The update includes a virtual movement of the first virtual object in a first direction and the second virtual object in a second direction opposite the first direction.

At step 1016, the diagnostic module receives input from a user. The input includes an indication of separation of the first virtual object and the second virtual object based on the virtual movement. The indication of separation comprises a relative virtual position between the first virtual object and the second virtual object where the user views the first virtual object and the second virtual object as separate objects.

At step 1018, the diagnostic module determines a first delta between the relative virtual position of the first virtual object and the second virtual object and an optimal virtual position.

At step 1020, the diagnostic module updates the rendering of the first virtual object and the second virtual object within the holographic display device. The update includes a virtual movement of the first virtual object in the second direction and the second virtual object in the first direction.

At step 1022, the diagnostic module receives a second input from the user. The input includes an indication of alignment of the first virtual object and the second virtual object based on the virtual movement. The indication of alignment comprises a relative virtual position between the first virtual object and the second virtual object where the user views the first virtual object and the second virtual object as aligned to appear as one virtual object.

At step 1024, the diagnostic module determines a second delta between the relative virtual position of the first virtual object and the second virtual object and an optimal virtual position.

Figure 10C:
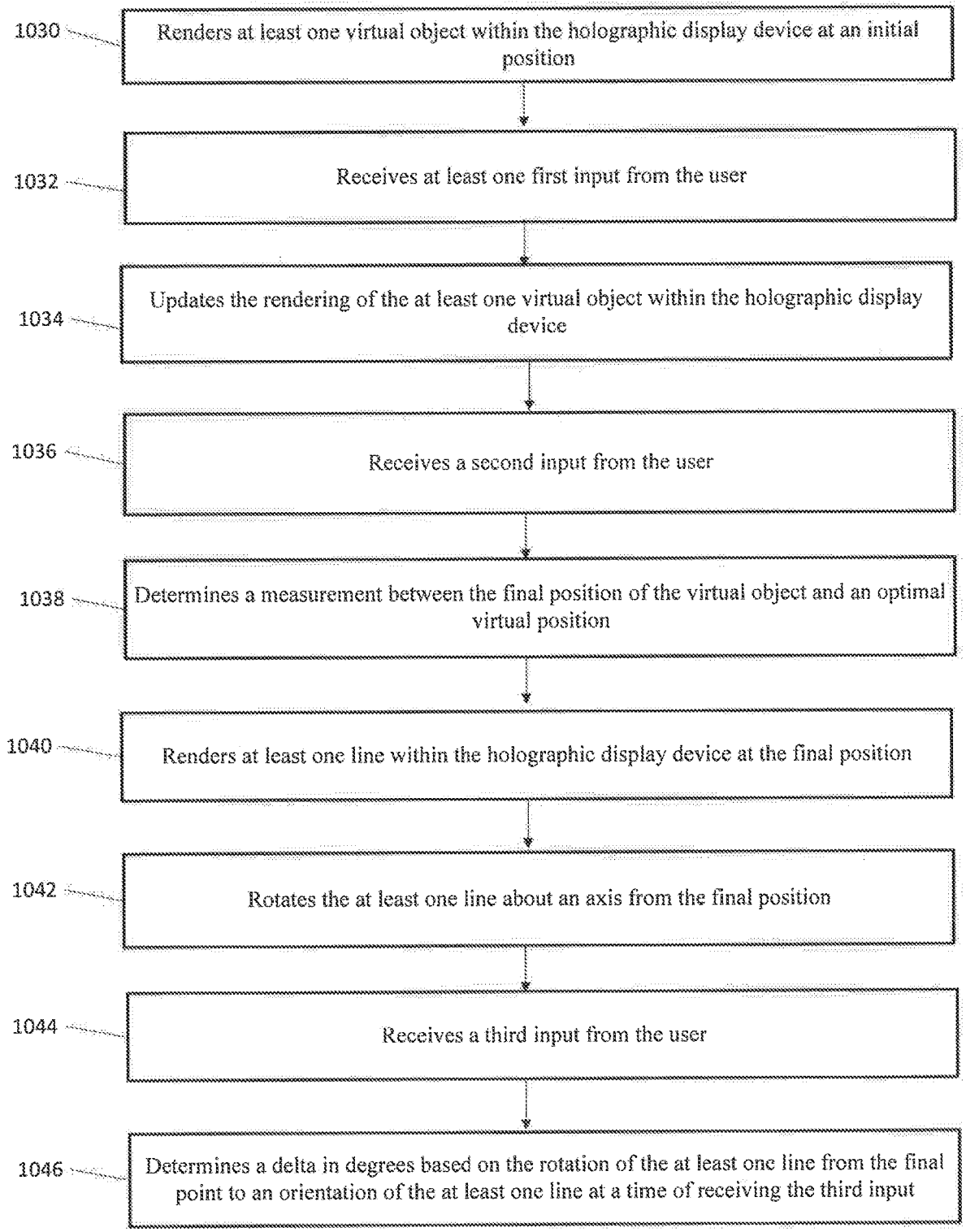

FIG. 10C illustrates a method for diagnosis and prescription of remedies for visual impairment in accordance with an exemplary embodiment.

At step 1030, the diagnostic module renders at least one virtual object within the holographic display device at an initial position. The rendering corresponds to a virtual level of depth corresponding to an initial simulated distance away from a user.

At step 1032, the diagnostic module receives at least one first input from the user. The at least one first input comprises an indication to move the at least one virtual object virtually towards or away from the user.

At step 1034, the diagnostic module updates the rendering of the at least one virtual object within the holographic display device. The update includes a virtual movement of the at least one virtual object in a direction towards or away from the user.

At step 1036, the diagnostic module receives a second input from the user. The second input includes an indication that the at least one virtual object appears clear to the user at a final position. The rendering corresponds to a virtual level of depth corresponding to a final simulated distance away from the user.

At step 1038, the diagnostic module determines a measurement between the final position of the virtual object and an optimal virtual position.

At step 1040, the diagnostic module renders at least one line within the holographic display device at the final position.

At step 1042, the diagnostic module rotates the at least one line about an axis from the final position.

At step 1044, the diagnostic module receives a third input from the user. The third input comprises an indication that the at least one line appears to the user to have rotated ninety degrees about the axis from the final position.

At step 1046, the diagnostic module determines a delta in degrees based on the rotation of the at least one line from the final point to an orientation of the at least one line at a time of receiving the third input.

Figure 10D:
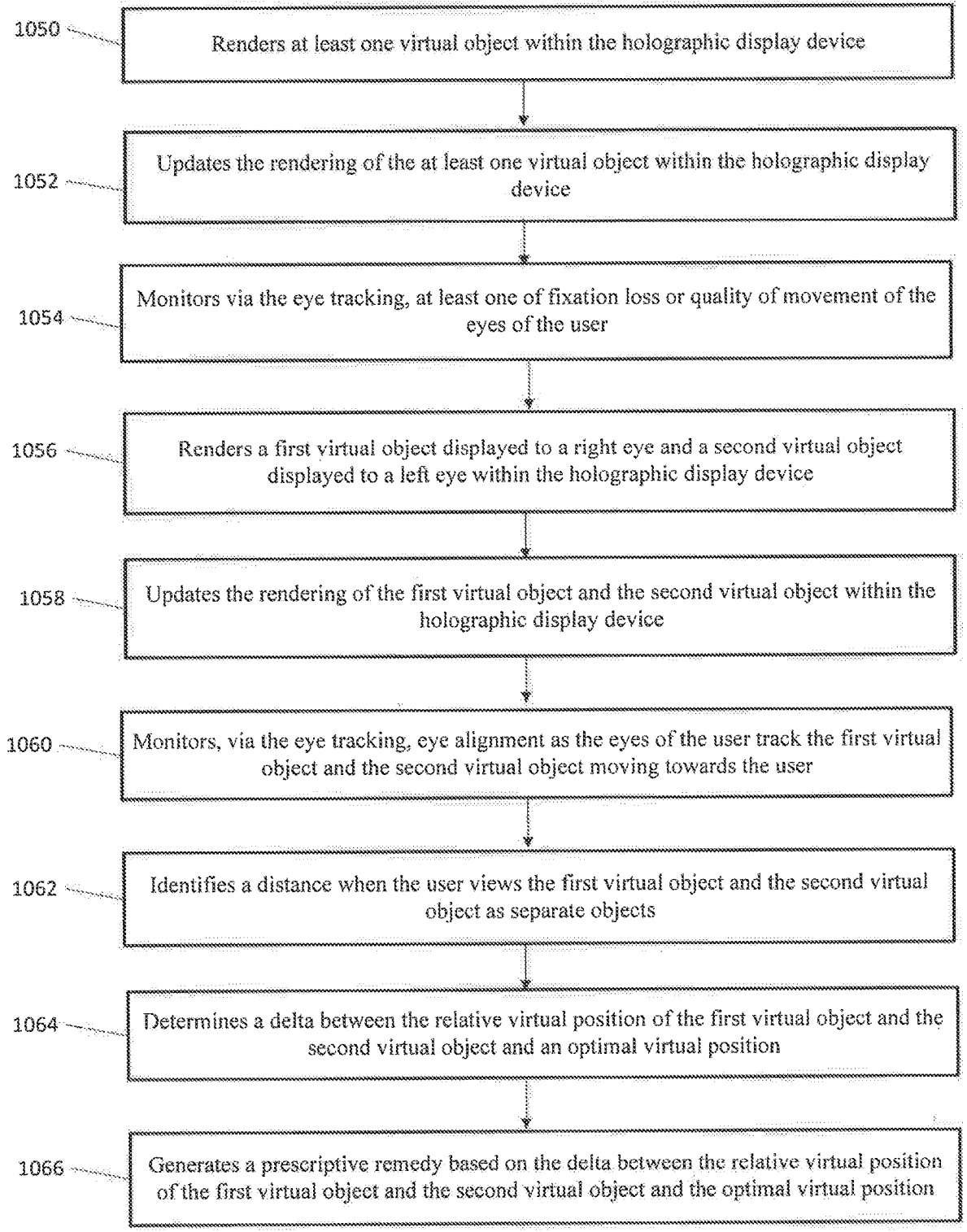

FIG. 10D illustrates a method for diagnosis and prescription of remedies for visual impairment in accordance with an exemplary embodiment.

At step 1050, the diagnostic module renders at least one virtual object within the holographic display device. The rendering corresponds to a virtual level of depth viewable by the user.

At step 1052, the diagnostic module updates the rendering of the at least one virtual object within the holographic display device. The update includes a virtual movement of the at least one virtual object within the virtual level of depth.

At step 1054, the diagnostic module monitors, via eye tracking, at least one of fixation loss or quality of movement of the eyes of the user.

At step 1056, the diagnostic module renders a first virtual object displayed to a right eye and a second virtual object displayed to a left eye within the holographic display device. The rendering corresponds to the first virtual object and the second virtual object aligned to appear as one virtual object to a user.

At step 1058, the diagnostic module updates the rendering of the first virtual object and the second virtual object within the holographic display device. The update includes a virtual movement of the first virtual object and the second virtual object towards the user.

At step 1060, the diagnostic module monitors, via the eye tracking, eye alignment as the eyes of the user track the first virtual object and the second virtual object moving towards the user.

At step 1062, the diagnostic module identifies a distance when the user views the first virtual object and the second virtual object as separate objects.

At step 1064, the diagnostic module determines a delta between the relative virtual position of the first virtual object and the second virtual object and an optimal virtual position.

At step 1066, the diagnostic module generates a prescriptive remedy based on the delta between the relative virtual position of the first virtual object and the second virtual object and the optimal virtual position.

Figure 11:
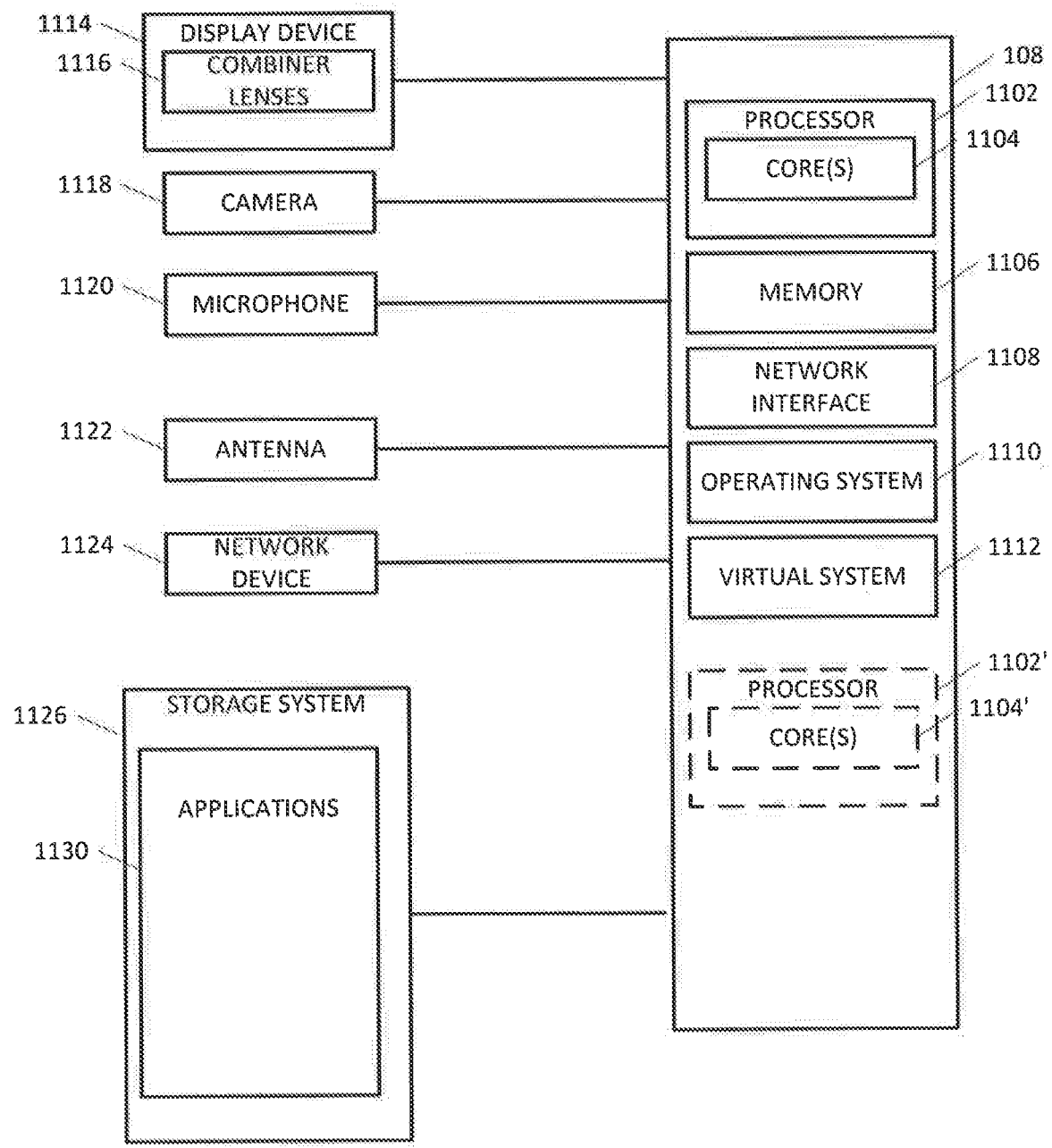
FIG. 11 depicts a block diagram an exemplary computing device in accordance with an exemplary embodiment.

FIG. 11 depicts a block diagram an exemplary computing device in accordance with an exemplary embodiment. Embodiments of the computing device 1100 can implement embodiments of the system including the holographic eye testing device. For example, the computing device can be embodied as a portion of the holographic eye testing device, and supporting computing devices. The computing device 1100 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 1106 included in the computing system 108 may store computer-readable and computer-executable instructions or software (e.g., applications 1130 such as rendering application) for implementing exemplary operations of the computing device 1100. The computing system 108 also includes configurable and/or programmable processor 1102 and associated core(s) 1104, and optionally, one or more additional configurable and/or programmable processor(s) 1102' and associated core(s) 1104' (for example, in the case of computer systems having multiple processors/cores), for executing computer-readable and computer-executable instructions or software stored in the memory 1106 and other programs for implementing exemplary embodiments of the present disclosure. Processor 1102 and processor(s) 1102' may each be a single core processor or multiple core (1104 and 1104') processor. Either or both of processor 1102 and processor(s) 1102' may be configured to execute one or more of the instructions described in connection with computing system 108.

Virtualization may be employed in the computing system 108 so that infrastructure and resources in the computing system 108 may be shared dynamically. A virtual machine 1112 may be provided to handle a process running on multiple processors so that the process appears to be using only one computing resource rather than multiple computing resources. Multiple virtual machines may also be used with one processor.

Memory 1106 may include a computer system memory or random access memory, such as DRAM, SRAM, EDO RAM, and the like. Memory 1106 may include other types of memory as well, or combinations thereof. The computing system 108 can receive data from input/output devices. A user may interact with the computing system 108 through a visual display device 1114, such as a combiner lenses 1116, which may display one or more virtual graphical user interfaces, a microphone 1120 and one or more cameras 1118.

The computing system 108 may also include one or more storage devices 1126, such as a hard-drive, CD-ROM, or other computer readable media, for storing data and computer-readable instructions and/or software that implement exemplary embodiments of the present disclosure. For example, exemplary storage device 1126 can include storing information associated with platform software and the application software.

The computing system 108 can include a network interface 1108 configured to interface via one or more network devices 1124 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing system can include one or more antennas 1122 to facilitate wireless communication (e.g., via the network interface) between the computing system 108 and a network and/or between the computing system 108 and other computing devices. The network interface 1108 may include a built-in network adapter, network interface card, PCMCIA network card, card bus network adapter, wireless network adapter, USB network adapter, modem or any other device suitable for interfacing the computing system 108 to any type of network capable of communication and performing the operations described herein.

The computing system 108 may run any operating system 1110, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing system 108 and performing the operations described herein. In exemplary embodiments, the operating system 1110 may be run in native mode or emulated mode. In an exemplary embodiment, the operating system 1110 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components, or method steps, those elements, components, or steps can be replaced with a single element, component, or step. Likewise, a single element, component, or step can be replaced with multiple elements, components, or steps that serve the same purpose. Moreover, while exemplary embodiments have been shown and described with references to particular embodiments thereof, those of ordinary skill in the art will understand that various substitutions and alterations in form and detail can be made therein without departing from the scope of the present disclosure. Further, still, other aspects, functions, and advantages are also within the scope of the present disclosure.

Exemplary flowcharts are provided herein for illustrative purposes and are non-limiting examples of methods. One of ordinary skill in the art will recognize that exemplary methods can include more or fewer steps than those illustrated in the exemplary flowcharts and that the steps in the exemplary flowcharts can be performed in a different order than the order shown in the illustrative flowcharts.

We claim:

1. An method for diagnosis and prescription of remedies for visual impairment, comprising:
   rendering, via a diagnostic module configured to execute on a computing device communicatively coupled to the head mounted holographic display device, a first virtual object displayed to the right eye and a second virtual object displayed to the left eye within a head mounted holographic display device, wherein the rendering corresponds to the first virtual object and the second virtual object aligned to appear as one virtual object to a user;
   updating, via the diagnostic module, the rendering of the first virtual object and the second virtual object within the holographic display device, wherein the updates comprise a virtual movement of the first virtual object in a first direction and the second virtual object in a second direction opposite the first direction;
   receiving, via the diagnostic module, input from a user, wherein the input comprises an indication of separation of the first virtual object and the second virtual object based on the virtual movement, wherein the indication of separation comprises a relative virtual position between the first virtual object and the second virtual object where the user views the first virtual object and the second virtual object as separate objects; and
   determining, via the diagnostic module, a first delta between the relative virtual position of the first virtual object and the second virtual object and an optimal virtual position.

2. The method of claim 1, further comprising:
   updating, via the diagnostic module, the rendering of the first virtual object and the second virtual object within the holographic display device, wherein the updates comprise a virtual movement of the first virtual object in the second direction and the second virtual object in the first direction;
   receiving, via the diagnostic module, a second input from the user, wherein the input comprises an indication of alignment of the first virtual object and the second virtual object based on the virtual movement, wherein the indication of alignment comprises a relative virtual position between the first virtual object and the second virtual object where the user views the first virtual object and the second virtual object as aligned to appear as one virtual object; and
   determining, via the diagnostic module, a second delta between the relative virtual position of the first virtual object and the second virtual object and an optimal virtual position.

3. The method of claim 2, further comprising generating, via the diagnostic module, a prescriptive remedy based on at least one of the first delta or the second delta.

4. The method of claim 1, wherein the input from the user comprises hand gestures and voice commands.

5. The method of claim 1, wherein the head mounted display device comprises a pair of transparent combiner lenses calibrated to the interpupillary distance.

6. The method of claim 1, wherein the first direction and the second direction are horizontal directions.

7. An apparatus for diagnosis and prescription of remedies for visual impairment, comprising:
   a head mounted holographic display device;
   a computing device communicatively coupled to the head mounted holographic display device;
   a diagnostic module configured to execute on the computing device, the diagnostic module when executed:
      renders a first virtual object displayed to the right eye and a second virtual object displayed to the left eye within the holographic display device, wherein the rendering corresponds to the first virtual object and the second virtual object aligned to appear as one virtual object to a user;
      updates the rendering of the first virtual object and the second virtual object within the holographic display device, wherein the updates comprise a virtual movement of the first virtual object in a first direction and the second virtual object in a second direction opposite the first direction;
      receives input from a user, wherein the input comprises an indication of separation of the first virtual object and the second virtual object based on the virtual movement, wherein the indication of separation comprises a relative virtual position between the first virtual object and the second virtual object where the user views the first virtual object and the second virtual object as separate objects; and
      determines a first delta between the relative virtual position of the first virtual object and the second virtual object and an optimal virtual position.

8. A method for diagnosis and prescription of remedies for visual impairment, comprising:
   rendering, via a diagnostic module configured to execute on a computing device communicatively coupled to a head mounted holographic display device, at least one virtual object within the holographic display device at an initial position, wherein the rendering corresponds to a virtual level of depth corresponding to an initial simulated distance away from a user;
   receiving, via the diagnostic module, at least one first input from the user, wherein the at least one first input comprises an indication to move the at least one virtual object virtually towards or away from the user;
   updating, via the diagnostic module, the rendering of the at least one virtual object within the holographic display device, wherein the updates comprise a virtual movement of the at least one virtual object in a direction towards or away from the user;
   receiving, via the diagnostic module, a second input from the user, wherein the second input comprises an indication that the at least one virtual object appears clear to the user at a final position, wherein the rendering corresponds to a virtual level of depth corresponding to a final simulated distance away from a user; and determining, via the diagnostic module, a measurement between the final position of the virtual object and an optimal virtual position.

9. The method of claim 8, further comprising:
rendering, via the diagnostic module, at least one line within the holographic display device at the final position;
rotating, via the diagnostic module, the at least one line about an axis from the final position;
receiving, via the diagnostic module, a third input from the user, wherein the third input comprises an indication that the at least one line appears to the user to have rotated ninety degrees about the axis from the final position; and
determining, via the diagnostic module, a delta in degrees based on the rotation of the at least one line from the final point to an orientation of the at least one line at a time of receiving the third input.

10. The method of claim 9, further comprising determining, via the diagnostic module, an axis and a cylinder power based on the delta.

11. The method of claim 9, wherein the at least one line corresponds to at least one concentric opaque ring across a surface of an invisible sphere.

12. The method of claim 9, further comprising:
shifting, via the diagnostic module, the at least one line 90 degrees from the axis to show an opposite side of the at least one line; and
receiving, via the diagnostic module, at least one fourth input from the user, wherein the at least one fourth input comprises an indication to move the at least one a line virtually towards or away from the user;
updating, via the diagnostic module, the rendering of the at least one line within the holographic display device, wherein the updates comprise a virtual movement of the at least one line in a direction towards or away from the user;
receiving, via the diagnostic module, a fifth input from the user, wherein the fifth input comprises an indication that the at least one line appears clear to the user.

13. The method of claim 8, further comprising determining, via the diagnostic module, a sphere power based on the measurement.

14. The method of claim 8, wherein the head mounted display device comprises a pair of transparent combiner lenses calibrated to the interpupillary distance.

15. An apparatus for diagnosis and prescription of remedies for visual impairment, comprising:
a head mounted holographic display device;
a computing device communicatively coupled to the head mounted holographic display device;
a diagnostic module configured to execute on the computing device, the diagnostic module when executed:
renders at least one virtual object within the holographic display device at an initial position, wherein the rendering corresponds to a virtual level of depth corresponding to an initial simulated distance away from a user;
receives at least one first input from the user, wherein the at least one first input comprises an indication to move the at least one virtual object virtually towards or away from the user;
updates the rendering of the at least one virtual object within the holographic display device, wherein the updates comprise a virtual movement of the at least one virtual object in a direction towards or away from the user;
receives a second input from the user, wherein the second input comprises an indication that the at least one virtual object appears clear to the user at a final position, wherein the rendering corresponds to a virtual level of depth corresponding to a final simulated distance away from a user; and
determines a measurement between the final position of the virtual object and an optimal virtual position.

16. A method for diagnosis and prescription of remedies for visual impairment, comprising:
rendering, via a diagnostic module configured to execute on a computing device communicatively coupled to a head mounted holographic display device enabled for eye tracking of eyes of a user, at least one virtual object within the holographic display device, wherein the rendering corresponds to a virtual level of depth viewable by the user;
updating, via the diagnostic module, the rendering of the at least one virtual object within the holographic display device, wherein the updates comprise a virtual movement of the at least one virtual object within the virtual level of depth; and
monitoring, via the diagnostic module, via the eye tracking, at least one of fixation loss or quality of movement of the eyes of the user.

17. The method of claim 16, further comprising the diagnostic module when executed:
rendering, via the diagnostic module, a first virtual object displayed to a right eye and a second virtual object displayed to a left eye within the holographic display device, wherein the rendering corresponds to the first virtual object and the second virtual object aligned to appear as one virtual object to a user;
updating, via the diagnostic module, the rendering of the first virtual object and the second virtual object within the holographic display device, wherein the updates comprise a virtual movement of the first virtual object and the second virtual object towards the user;
monitoring, via the diagnostic module, via the eye tracking, eye alignment as the eyes of the user track the first virtual object and the second virtual object moving towards the user;
identifying, via the diagnostic module, a distance when the user views the first virtual object and the second virtual object as separate objects;
determining, via the diagnostic module, a delta between the relative virtual position of the first virtual object and the second virtual object and an optimal virtual position; and
generating, via the diagnostic module, prescriptive remedy based on the delta between the relative virtual position of the first virtual object and the second virtual object and the optimal virtual position.

18. The method of claim 16, wherein the rendering of the at least one virtual object within the holographic display device comprises virtually moving the at least one virtual object from left to right, right to left, a circle clock wise, and a circle counter-clockwise.

19. The method of claim 16, wherein the head mounted display device comprises a pair of transparent combiner lenses calibrated to the interpupillary distance.

20. An apparatus for diagnosis and prescription of remedies for visual impairment, comprising:
- a head mounted holographic display device enabled for eye tracking of eyes of a user;
- a computing device communicatively coupled to the head mounted holographic display device;
- a diagnostic module configured to execute on the computing device, the diagnostic module when executed:
  - renders at least one virtual object within the holographic display device, wherein the rendering corresponds to a virtual level of depth viewable by the user;
  - updates the rendering of the at least one virtual object within the holographic display device, wherein the updates comprise a virtual movement of the at least one virtual object within the virtual level of depth; and
  - monitors, via the eye tracking, at least one of fixation loss or quality of movement of the eyes of the user.

* * * * *